United States Patent
Mensinger et al.

(10) Patent No.: US 10,945,600 B2
(45) Date of Patent: Mar. 16, 2021

(54) SYSTEMS AND METHODS FOR DISTRIBUTING CONTINUOUS GLUCOSE DATA

(71) Applicant: DexCom, Inc., San Diego, CA (US)

(72) Inventors: Michael Robert Mensinger, San Diego, CA (US); Esteban Cabrera, Jr., San Diego, CA (US); Eric Cohen, San Diego, CA (US); Nathaniel David Heintzman, San Diego, CA (US); Apurv Ullas Kamath, San Diego, CA (US); Gary A. Morris, La Jolla, CA (US); Andrew Attila Pal, San Diego, CA (US); Eli Reihman, San Diego, CA (US); Jorge Valdes, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1115 days.

(21) Appl. No.: 15/019,881

(22) Filed: Feb. 9, 2016

(65) Prior Publication Data
US 2016/0232318 A1 Aug. 11, 2016

Related U.S. Application Data

(63) Continuation of application No. 15/019,807, filed on Feb. 9, 2016, now abandoned.
(Continued)

(51) Int. Cl.
*A61B 5/00* (2006.01)
*G06F 21/62* (2013.01)
(Continued)

(52) U.S. Cl.
CPC .......... *A61B 5/0002* (2013.01); *A61B 5/0004* (2013.01); *A61B 5/0022* (2013.01);
(Continued)

(58) Field of Classification Search
CPC ........ G16H 10/60; G16H 10/65; G16H 40/67; G06F 21/62; G06F 21/602;
(Continued)

(56) References Cited

U.S. PATENT DOCUMENTS 5,924,074 A    7/1999  Evans
8,582,421 B2   11/2013 Sloan
(Continued)

FOREIGN PATENT DOCUMENTS

CN    102841976 A    12/2012
CN    103260514 A    8/2013
(Continued)

OTHER PUBLICATIONS

Office Action for Chinese Application No. 201680036366.7 dated Sep. 1, 2020, 12 pages—. (no Translation available).
(Continued)

*Primary Examiner* — John P Go
(74) *Attorney, Agent, or Firm* — Knobbe, Martens, Olson & Bear, LLP

(57) ABSTRACT

The present disclosure relates to systems, devices and methods for receiving biosensor data acquired by a medical device, e.g., relating to glucose concentration values, and controlling the access and distribution of that data. In some embodiments, systems and methods are disclosed for monitoring glucose levels, displaying data relating to glucose values and metabolic health information, and controlling distribution of glucose data between applications executing on a computer, such as a smart phone. In some embodiments, systems and methods are disclosed for controlling access to medical data such as continuously monitored glucose levels, synchronizing health data relating to glucose levels between multiple applications executing on a computer, and/or encrypting data.

27 Claims, 19 Drawing Sheets

Related U.S. Application Data

(60) Provisional application No. 62/114,386, filed on Feb. 10, 2015, provisional application No. 62/269,035, filed on Dec. 17, 2015.

(51) Int. Cl.

| | | |
|---|---|---|
| *G06F 21/60* | (2013.01) | |
| *G16H 10/60* | (2018.01) | |
| *G16H 50/30* | (2018.01) | |
| *A61B 5/145* | (2006.01) | |
| *G16H 40/67* | (2018.01) | |

(52) U.S. Cl.
CPC ........ *A61B 5/14532* (2013.01); *A61B 5/7275* (2013.01); *A61B 5/742* (2013.01); *G06F 21/602* (2013.01); *G06F 21/62* (2013.01); *G06F 21/6245* (2013.01); *G16H 10/60* (2018.01); *G16H 40/67* (2018.01); *G16H 50/30* (2018.01)

(58) Field of Classification Search
CPC ............... G06F 21/6245; A61B 5/0002; A61B 5/14532; A61B 5/0004; A61B 5/0022; A61B 5/742; A61B 5/7275
See application file for complete search history.

(56) References Cited

U.S. PATENT DOCUMENTS

| | | | |
|---|---|---|---|
| 9,160,834 B2 | 10/2015 | Yarger et al. | |
| 2003/0208113 A1 | 11/2003 | Mault et al. | |
| 2006/0272652 A1 | 12/2006 | Stocker et al. | |
| 2007/0214495 A1* | 9/2007 | Royer ..................... | H04L 63/12 726/2 |
| 2009/0036753 A1* | 2/2009 | King .................. | A61B 5/14532 600/301 |
| 2009/0099864 A1* | 4/2009 | Cronrath .................. | G06F 8/60 705/2 |
| 2009/0113295 A1 | 4/2009 | Halpern et al. | |
| 2009/0150172 A1* | 6/2009 | Duffey-Rosenstein ...................... | G06Q 10/1095 705/2 |
| 2009/0192366 A1* | 7/2009 | Mensinger ............. | A61B 5/743 600/301 |
| 2009/0222539 A1* | 9/2009 | Lewis ..................... | G16H 40/20 709/221 |
| 2010/0292556 A1* | 11/2010 | Golden .................. | G16H 40/40 600/364 |
| 2010/0298685 A1 | 11/2010 | Hayter et al. | |
| 2011/0058485 A1 | 3/2011 | Sloan | |
| 2011/0201911 A1* | 8/2011 | Johnson ............... | A61B 5/0004 600/365 |
| 2012/0144407 A1* | 6/2012 | Hacigumus ........... | G06F 9/5072 719/328 |
| 2012/0245446 A1* | 9/2012 | Amann-Zalan ..... | G06F 19/3481 600/365 |
| 2013/0164718 A1 | 6/2013 | Buck et al. | |
| 2013/0172688 A1 | 7/2013 | Allen et al. | |
| 2014/0106676 A1 | 4/2014 | Yarger et al. | |
| 2014/0166676 A1 | 6/2014 | Melrose | |
| 2016/0232322 A1 | 8/2016 | Mensinger et al. | |

FOREIGN PATENT DOCUMENTS

| | | | |
|---|---|---|---|
| CN | 103930029 A | 7/2014 | |
| CN | 104137108 A | 11/2014 | |
| EP | 1154718 A1 | 11/2001 | |
| EP | 1154718 B2 | 11/2001 | |
| WO | WO-2012164166 A1 * | 12/2012 | ........... H04L 63/102 |
| WO | WO 2014/105631 | 7/2014 | |

OTHER PUBLICATIONS

International Preliminary Report on Patentability for Application No. PCT/US2016/017137 dated Aug. 24, 2017, 12 pages.
International Search Report and Written Opinion for Application No. PCT/US2016/017137 dated Aug. 8, 2016, 16 pages.
Office Action for Japanese Application No. 2017-538377, dated Jun. 8, 2020, 6 pages.

* cited by examiner

SYSTEMS AND METHODS FOR DISTRIBUTING CONTINUOUS GLUCOSE DATA

INCORPORATION BY REFERENCE TO RELATED APPLICATIONS

Any and all priority claims identified in the Application Data Sheet, or any correction thereto, are hereby incorporated by reference under 37 CFR 1.57. This patent application is a continuation of U.S. patent application Ser. No. 15/019,807, filed on Feb. 9, 2016, which claims the benefit of U.S. Provisional Patent Application No. 62/114,386, filed on Feb. 10, 2015, and U.S. Provisional Patent Application No. 62/269,035, filed on Dec. 17, 2015. The disclosure of each of the foregoing applications is hereby expressly incorporated by reference herein in its entirety and is hereby expressly made a portion of this application.

TECHNICAL FIELD

The present disclosure relates to a continuous glucose monitor for wirelessly transmitting data relating to glucose values, and controlling the display and distribution of that data.

BACKGROUND

Continuous glucose monitors have been increasing in popularity as an easy way to monitor glucose levels. In the past, patients sample their blood glucose levels several times throughout a day, such as in the morning, around lunch, and in the evening. The levels can be measured by taking a small blood sample of the patient and measuring the glucose levels with a test strip or glucose meter. This technique, however, has drawbacks because patients would prefer to not have to take a blood sample, and users do not know what their blood glucose levels are throughout the day between the samples.

One potentially dangerous timeframe is at night because a patient's glucose levels can fall dangerously low during sleep. As a result, continuous glucose monitors have gained popularity by providing a sensor that continuously measures glucose levels of a patient and transmits the measured glucose levels wirelessly to a display. This allows the patient or patient's caregiver to monitor the patient's glucose levels throughout the day and even set alarms for when glucose levels reach a predefined level or experience a defined change.

Initially, continuous glucose monitors wirelessly transmitted data relating to glucose levels to a dedicated display. The dedicated display is a medical device designed to display glucose levels, trending patterns, and other information for a user. However, with the increasing popularity of smart phones and applications executing on smart phones, some users prefer to avoid having to carry a dedicated display. Instead, some users prefer to monitor their glucose levels using an application executing on a smart phone.

A computing device executing an application can communicate with a continuous glucose monitor and display glucose levels and other information. In addition, the computing device executing an application can share glucose levels with other applications, servers, or devices in a cloud computing infrastructure. In one example, a computing device and the application can share their glucose levels with another smart phone or other computing device executing an application for overall health monitoring. Sharing or retransmitting medical data, whether to another application, device, or server, presents risks due to the possibility that the medical data may be compromised or used improperly. The additional applications may provide incorrect recommendations to a user, or retransmit sensitive medical information to additional devices or applications, leading to a breach of patient confidentiality.

The present disclosure is directed to overcoming these and other problems.

SUMMARY

Certain embodiments of the present disclosure generally relate to techniques for controlling and protecting retransmission of patient medical data. In an illustrative embodiment, a medical device, such as a continuous glucose sensor, transmits medical data to a computing device executing a software application, e.g., such as a smart phone, tablet, smartwatch, or other wearable and/or mobile computing device. The computing device executing the software application, illustratively described as a smart phone, can control the redistribution and use of this medical data. The redistribution may be to one or more third-party applications running on the smart phone, or to remote computing devices, such as a server or to a separate smart device. A set of controls operate to limit the ability of separate applications to obtain or use the medical data outside of the intended uses. In one exemplary embodiment, the medical data can be delayed before providing it to other software applications on the computing device or other computing devices executing applications or devices to control use of third-party recommendations in a situation that could pose an immediate health risk. In other exemplary embodiments, the medical data can be encrypted to control access to the medical data by other applications and devices. Devices that are authorized to use the medical data can receive a key to decrypt all or some of the data. In another exemplary embodiment, software executing on the continuous glucose monitor or display separates out a subset of the medical data, such as data that poses fewer risks of compromising patient confidentiality, and provides the reduced set of data to additional applications and devices. These embodiments, as well as others described in more detail below, protect patient confidentiality and control the redistribution of medical data.

For example, certain embodiments address a number of issues that arise relating to providing glucose levels to different applications executing on computing devices, such as a smart phone. For example, a third-party can create an application that accesses the data relating to glucose levels. The third-party application may use the accessed data to provide warnings to a user, such as when glucose levels fall too low or rise too high. However, the third-party application does not properly account for calibration levels and correct correspondence between the wirelessly transmitted data and actual glucose levels. As a result, for example, the third-party application could incorrectly calculate glucose levels based on the received data and notify a user (e.g., a patient or patient's monitor) that the patient's glucose levels are too high or low when the levels are in fact within an acceptable range, or even worse, the third-party application could indicate a patient's monitored glucose level is within an acceptable glucose range but in fact the patient's glucose level is dangerously low. Also, for example, the third-party applications may improperly identify trends or miss alarms based on monitored glucose levels because the developer of the application did not properly set up the application to account for important glucose clinical risk factors. Also, for example, the third-party applications may fail to notify the user when the patient's levels have entered a dangerous range due to a bug in the software or the developer was not knowledgeable about appropriate glucose clinical risk levels. Accordingly, exemplary embodiments control display and use of medical data by applications.

In addition, third-party applications may not have been submitted to the U.S. Food and Drug Administration for approval. Obtaining approval for a medical device is a timely and costly process. Unapproved applications often suffer security flaws that are unacceptable for sensitive medical data. For example, a user allows a third-party application to access data relating to glucose levels, but then is unaware that the allowed application also provides the data to additional third-party applications. These additional third-party applications might distribute the medical data to additional applications, internet servers, or data repositories without full knowledge by the user. This creates a serious security risk that medical data can be compromised and sent to unauthorized parties. Accordingly, certain embodiments control distribution of medical data between applications. In particular, the continuous glucose sensor or software executing on the display can encrypt data before distributing it to other third-party applications.

While aware of risks associated with using applications executing on computing devices such as a smart phone to monitor medical information, using smart phones to monitor health information can result in a more complete view of a user's health. Many applications are available for smart phones that monitor health information. Some of this information can have a direct impact on a user's glucose levels. For example, a user installs an application on their smart phone that records exercising activity. Exercising has a direct impact on glucose levels. As a result, exemplary embodiments integrate health information from other applications with data relating to glucose levels on a single display. This allows a user to conveniently determine activities that impact their glucose levels and the extent of impact.

An additional issue with using applications executing on computing devices that can display data relating to glucose levels, such as a smart phone, is how to handle missed data. A transmitter can continuously, or periodically, transmit data relating to glucose levels, but a user may have turned their smart phone off, run out of battery, or left it out of the range of transmissions. When the user executes the application, it will be missing the data that was not received because the smart phone was off or out of range. This can cause confusion to a user who sees old data displayed. As a result, in some embodiments, backfill data is provided to the application that did not receive the data, e.g., due to discontinuity in communications between the transmitter and the application executing on the computing device. This can allow the user to see historical trending data for their glucose levels even when transmissions were missed.

In one example embodiment of the disclosed technology, a method for monitoring glucose values includes receiving, at a first application operable on a mobile computing device, health data including a glucose measurement and associated timestamp transmitted over a wireless connection; determining, by the first application, that a time duration between a current time and the timestamp meets a predetermined amount of delay; and providing, by the first application, the glucose measurement to a second application operable on the mobile computing device only after the predetermined amount of delay.

In another example embodiment of the disclosed technology, a system for monitoring glucose values includes a sensor configured to obtain a glucose measurement of an amount of glucose; a wireless transmitter to transmit the glucose measurement and a timestamp associated with the glucose measurement; and a mobile computing device, comprising a wireless receiver configured to receive the glucose measurement, a memory to store data including the received glucose measurement, a processor to process the data, and a first software application including instructions stored in the memory which, when executed by the processor, determines when a time duration between a current time and the timestamp meets a predetermined amount of delay, and upon determination the time duration meets the predetermined amount of delay, provides the glucose measurement to a second software application on the mobile computing device, in which the second software application is operable to receive the glucose measurement when provided by the first software application after the predetermined amount of delay.

In another example embodiment of the disclosed technology, a medical device software application for managing glucose data received from a glucose sensor is disclosed. The medical device software application is on a computer-readable medium of a mobile computing device, and includes instructions which, when executed by a processor of the mobile computing device, causes the mobile computing device to receive one or more glucose measurements generated by the glucose sensor, wherein the one or more glucose measurements include an associated timestamp; assign the received one or more glucose measurements as retrospective glucose data or actionable glucose data based on a predetermined amount of time difference between the timestamp and a current time; and provide the retrospective glucose data measurement to a third-party application operable on the mobile computing device.

Other systems, methods, features and/or advantages will become apparent to one with skill in the art upon examination of the following drawings and detailed description. It is intended that all such additional systems, methods, features and/or advantages be included within this description and be protected by the accompanying claims.

DETAILED DESCRIPTION

Figure 1:
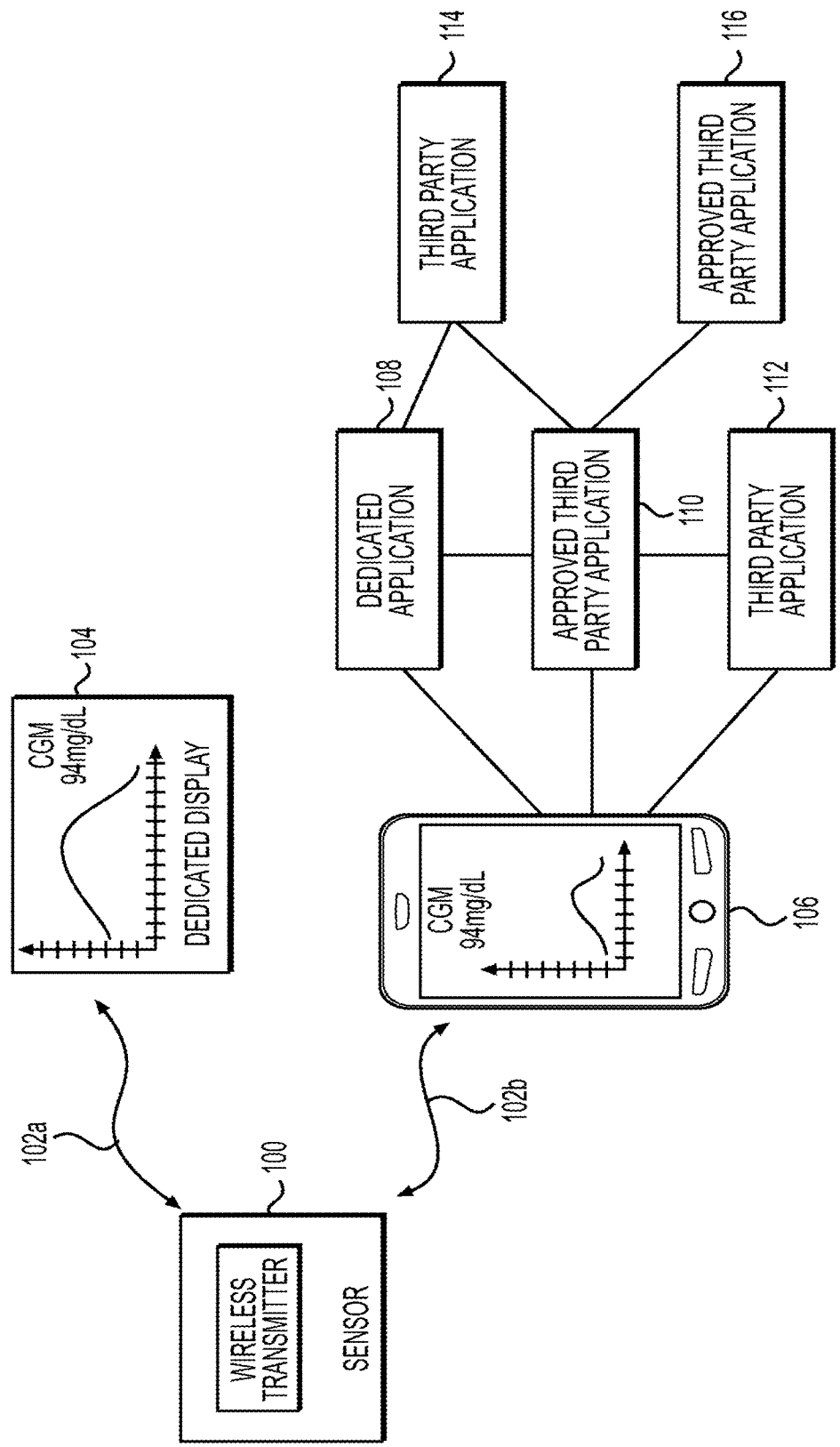
FIG. 1 illustrates an exemplary system for monitoring glucose levels.

Illustrative embodiments described in the present disclosure relate to techniques for receiving glucose data from a continuous glucose sensor and controlling the use and redistribution of that data so it is used in an intended manner. Some embodiments control which applications will receive the data, provide security measures for maintaining the privacy of medical data, and display glucose levels and other health information for applications executing on a smart phone, among other things. Embodiments therefore provide users with the convenience of accessing medical data, such as glucose levels, on a smart phone, while maintaining privacy and security when redistributing medical data to other applications and devices. Although certain embodiments are described as displaying medical data on a smart phone, it is understood that other display devices, including a tablet, personal computer, smart watch, cloud application, and the like can be used.

An example environment will now be discussed to illustrate some embodiments disclosed herein.

The example environment generally involves a networked system of one or more body-worn medical devices that measure one or more health characteristics of a patient and/or administer one or more treatments to the patient communicating with electronic device(s). The monitored health characteristics can include the glucose concentration of the host in this example, but can instead or additionally be any one or more of other health characteristics described herein. The treatment administered to the patient can include administering insulin using an insulin pump, for example, but can be any one or more of other treatments described herein in other examples.

Further to the example environment, the one or more body-worn medical devices can each generate data and provide the data to a consumer electronics device, such as a smart phone, tablet, smartwatch, or other wearable and/or mobile computing device. A smart phone is used in the following example and other examples described. The smart phone can include a dedicated application that configures the smart phone to receive and process the data provided (e.g., wirelessly transmitted) by the body-worn medical devices. The data provided by the body-worn medical devices can include glucose measurements, insulin delivery amounts, diagnostic information about the medical devices and timestamps associated with each, for example. The smart phone, using the dedicated application, can then perform various functions based on the received data, such as generate charts and user perceptible-alarms using the data. The smart phone, using the dedicated application, may also receive and generate other data, such as data from a user of the smart phone (e.g., user identifying information), user interactions with the dedicated application, dedicated application diagnostic information, and the like. In some embodiments, the dedicated application may include a suite of dedicated applications operable on one or more computing devices of a patient user and/or of non-patient users to manage access to the patient user's data acquired by the medical device. In one example, the suite of dedicated applications can include a first dedicated application operable on the patient user's smart phone to process and provide biomedical data to the patient user wearing the body-worn medical device, a second dedicated application operable on the patient user's smart phone to provide the patient user with control of how the biomedical data may be shared with others (e.g., remote monitors), and/or a third dedicated application operable on another user's device (e.g., remote monitor's smart phone) to remotely monitor authorized data from the biomedical data.

The dedicated application can be one or more applications downloaded from a remote server using the smart phone. In one example, the smart phone is an iPhone commercially available from Apple, Inc. and the application is a so-called "App" downloaded from the App Store commercially operated by Apple, Inc.

It may also be desirable for the dedicated application to provide some or all of the body-worn medical device generated data and dedicated application generated data to other applications (e.g., third-party application(s)) resident on the smart phone or other communicatively connected computing system, such as a third party's smart phone (e.g., caretaker or family member) or company system (e.g., electronic health records operated by the Mayo Clinic located in Rochester, Minn. or Epic located in Verona, Wis.). The third-party application may have other capabilities that provide advantages to the user over the dedicated application, such as being able to process the provided data in a different way (e.g., has more processing power or capability to generate different, useful charts or insights) and/or integrate the provided data with other data (e.g., integrate glucose and insulin data provided by the dedicated application with meal data and exercise data generated by the third-party application).

In this exemplary environment, the dedicated application provides either all or select data to a distribution application running on the smart phone. The distribution application functions to facilitate distribution of the data collected from and generated by the dedicated application to other application(s) running on the smart phone. The distribution application can be another so-called "App" running on the smart phone. The distribution application can include an application programming interface (API) that allows other applications, such as the dedicated application and third-party applications resident on the smart phone, to provide data and access data from the distribution application. In this manner, the dedicated application can provide data to the distribution application, which is then available to third-party applications on the smart phone. These third-party applications can obtain, process and output the data in any way the application is capable. As a specific example, the third-party application can include meal tracking functionality that obtains glucose generated data provided by the dedicated application via the distribution application. The third-party application can integrate the glucose data with meal information to provide valuable insights to the user, so as correlating meals with fluctuations of the user's glucose levels.

However, it may be desirable to limit the data to which the third-party applications have access, in some implementations. For instance, users may not want some or all third-party applications to have access to confidential information, such as patient identifiable information. Or certain types of information may be more highly controlled by government regulations, e.g., in particular certain types of medical information that the government regulations prohibit other applications to access absent those applications having been approved by the relevant government body. Further, safety considerations may be a factor in limiting what applications can access data. For instance, even if regulations do not prohibit exchanging data, it may be desirable to limit access of certain types of data so third-party applications do not use the data in an unsafe way, such as incorrectly prompting a user to undertake a clinically dangerous medical action.

Accordingly, the exemplary embodiments in this exemplary environment can limit the distribution of data to third-party applications. In some implementations, only certain types of data are provided to the distribution application, so that the third-party applications cannot at least directly access that data. In some implementations, some or all data is encrypted prior to providing the data to the distribution application. In this way, only third-party applications that have a key to decrypt the encrypted data can use the encrypted data accessed from the distribution application. Such a key can be provided only to approved third-party applications that have satisfied regulatory and/or safety requirements in some implementations. Other ways of limiting access to some or all data may be used as well or instead as described elsewhere herein.

Further to the exemplary environment, it may be desirable to limit third-party application access of health measurement data to so-called retrospective measurement data. Retrospective measurement data is data that is no longer actionable data. That is, actionable data is data that can be used with timeliness sufficient to allow effective action to prevent or respond to an adverse change in physiological state of a patient. Actionable data is so-called real-time continuous glucose measurements and can also include predicted continuous glucose measurements (e.g., glucose values predicted for a future period in time, such as 5 minutes or an hour into the future). To illustrate with an example of glucose data, actionable continuous glucose measurement data is glucose measurement data that can be used to treat a current clinical diabetic state of a patient, such as impending or actual hypoglycemia, or impending or actual hyperglycemia. In contrast, retrospective continuous glucose data is data that would not be used for treating a current clinical state of a user because the data is likely too old to provide value for formulating decisions on how to treat the patient. While not necessarily useful for treating a current clinical state, retrospective data is still very useful for extrapolating insights into a patient's health. Examples include comparing glucose levels of a patient over time to carbohydrates ("carbs") and/or medication ingested by the patient to gain insights as to how the carbs and/or medication have been affecting the patient's glucose levels, and perhaps modify a treatment plan of associated with the patient.

It is understood that what constitutes actionable data may depend upon various factors. For instance, what constitutes actionable data may depending upon how quickly a clinical state of a health condition associated with one or more monitored health characteristics can change from a non-adverse physiological state to an adverse physiological state. To illustrate, although diabetic clinical states can change relatively quickly—for example, from being in safe range of glucose concentration to an unhealthy range of glucose concentration the timeframe for such a change is typically in the order of longer than about 30 minutes. In contrast, a monitored health condition associated with a heart condition can change much quicker, in the order of minutes or even seconds. Thus, actionable data associated with monitoring a diabetic condition (e.g., continuous glucose data) may extend along a longer timeframe than data associated with monitoring a heart condition (e.g., EKG and heart rate data).

Accordingly, in the above exemplary environment, retrospective glucose data can be accessed by third-party applications from the dedicated application via the distribution application, as discussed above, but third-party applications are prevented from accessing non-retrospective glucose data, such as actionable and predicted glucose data.

In some implementations, for example, retrospective data is data indicative of a monitored health characteristic of a host that is older than one of 1 minute, 5 minutes, 15 minutes, 30 minutes, 1 hour, 3 hours, 5 hours 12 hours, 24 hours or 1 day. For instance, in one embodiment of monitoring a glucose level of a host, continuous glucose data older than 3 hours is considered retrospective glucose data. In contrast, continuous glucose data measured within the last three hours is considered non-retrospective data, including actionable data.

The following are further detailed examples that may include some of the previously-noted features of the example environment, but need not necessarily include any of the previously-noted features.

FIG. 1 illustrates an exemplary system for monitoring glucose levels and controlling access to and use of medical data. With reference to FIG. 1, continuous glucose sensor unit 100 obtains a series of measurements relating to glucose levels in a user. The continuous glucose sensor unit 100 can be worn, for example, in the abdomen region of a patient. A small sensor can extend into the patient to obtain readings of glucose values using, for example, subcutaneous glucose or blood glucose readings. The continuous glucose sensor unit 100 can also be a transdermal device, an intravascular device, or a non-invasive device.

Continuous glucose sensor unit 100 can include a number of components to obtain glucose measurements, store the data, calculate glucose levels, communicate with a dedicated display 104 and/or other computing device 106 (such as a smart phone, and referred to herein for convenience as display 106), and perform other tasks. For example, although not illustrated, continuous glucose sensor unit 100 can include nonvolatile memory for storing historical data regarding glucose values, a processor, a battery, and a wireless transmitter. The wireless transmitter provides any type of wireless communications 102a and 102b, e.g., including a Bluetooth connection (e.g., low energy Bluetooth (BLE)), Wi-Fi connection, RF connection, and others. The wireless communications 102a and 102b occur, in some embodiments, between paired, authenticated devices, and use encryption and other cryptographic techniques to ensure that communications remain confidential.

While illustrated as a single unit, portions of the sensor unit 100 may be removable from remaining portions of the continuous glucose sensor unit. For example, reusable electronics portions of the sensor unit 100 (e.g., transmitter, battery, memory) may be removable from single use portions of the sensor unit (e.g., and reused with a new single use portion). Further, the continuous glucose sensor unit 100 can include other components to facilitate data communications. For example, the continuous glucose sensor unit 100 may include wired ports, such as a USB port, Ethernet port, and others, for communicating with other devices and providing data relating to glucose levels, system data, etc.

The continuous glucose sensor unit 100 of FIG. 1 obtains samples at predetermined intervals, such as every few seconds, every thirty seconds, every minute, every five minutes, or on demand in response to the occurrence of an event (e.g., a command from a user, detection of a user action, such as user movement, and the like). The wireless transmitter can be turned off or put into a low power state to conserve battery life while one or more measurement are taken over a period of time, and then wake the transmitter back up to wirelessly transmit the one or more measurements to dedicated display 104 and/or display 106 in a batch transfer. For example, the continuous glucose sensor unit 100 can wake up the wireless transmitter every five minutes, transfer data relating to glucose measurements (and any other data) generated over the last five minutes, and transfer the data to the dedicated display 104 and/or display 106. The wireless transmitter can then be turned off again to conserve battery life. While an example of transferring data every five minutes has been provided, it will be appreciated that longer or shorter time periods can be used, and the time period can be configured by a user via the dedicated display 104 or/or the display 106.

The data transmitted between continuous glucose sensor unit 100 and dedicated display 104 and/or display 106 can be any type of data relating to monitoring glucose values and the operation of the continuous glucose sensor unit. For example, the continuous glucose sensor unit 100 exchanges calibration data with dedicated display 104 and/or 106 on initial startup and periodically to maintain accuracy of the glucose measurements. A user samples their glucose level using a single point glucose meter, enters the value displayed by the test kit into one of displays 104 and 106, and that value calibrates the continuous glucose sensor unit 100. Other examples of data exchanged include an amount of current or voltage measured by continuous glucose sensor, a converted glucose value in, for example, mg/dL, and a timestamp associated with the time when each measurement or value was sampled, alerts related to glucose levels exceeding predetermined thresholds, detected faults in the system, and the like. Although described as a continuous glucose sensor unit 100, other medical devices may be used with the disclosed embodiments. For example, the continuous glucose sensor unit 100 can be an analyte sensor and the transmitted data can reflect analyte values.

Dedicated display 104 can be a display dedicated to use with continuous glucose sensor unit 100. The combination of the continuous glucose sensor unit 100 and dedicated display 104 can, in one embodiment, be an approved medical device, such as a class III medical device. Dedicated display 104 receives data relating to glucose levels from continuous glucose sensor unit 100 at predetermined time intervals. In some embodiments, dedicated display 104 can include a dedicated application 108 to receive and display at least a portion or the entire set of data received from continuous glucose sensor unit 100. For example, the dedicated display 104 displays actual glucose levels associated with measurements taken by the sensor. In some embodiments, the display 104 may be a designed to receive, process, and/or store the data but have a limited user interface, such as limited user functionality or a small display configured to display limited information (e.g., such as a recently measured analyte concentration value and a trend arrow). In some examples, the user interface of display 104 can include a reduced amount of input buttons (e.g., physical buttons or virtual buttons on an interactive display screen) to allow the user to input information (e.g., such as calibration information, including glucose concentration values from a single point blood glucose device, and/or settings for alarms, rules, etc.). In some examples, the display 104 can include an audible alarm and/or a vibrator motor alarm. By keeping the functionality of the display 104 limited, the display 104 may be easily carried by the user, yet provide the user with an interactive device to track and inform the user of their monitored glucose information (from the sensor unit 100) and provide other important health information and alerts without the need of a larger, secondary computing device. The display 104 can be coupled to another computing or display device (e.g., display 106) to display enhanced glucose and health related information that the user may want to view, such as detailed reports based on a retrospective analysis of the data.

In some embodiments, the display 106 can include a dedicated application 108 to receive and display at least a portion or the entire set of data received from continuous glucose sensor unit 100. The display 106 can include one or more third-party applications such as approved third-party application 110 (approved to manage health data) and/or other third-party application 112 (not approved to manage health data) to be provided or allowed access to certain data received from continuous glucose sensor unit 100. In some embodiments, the transmitter of the sensor unit 100, an operating system executing on the display 106, or the dedicated application 108 operating on the display 106 can restrict third-party applications from receiving and displaying actual glucose levels. The third-party applications instead can receive a more generic indicator of glucose levels, such as whether glucose levels are low, normal, or high. Additional details regarding the types of data that can be sent to and displayed by the dedicated display 104 and the display 106 will be provided below.

Dedicated display 104 includes a processor for calculating glucose levels based on received measurements, memory for storing glucose levels, ports for wired communications, and wireless communication circuits, such as Bluetooth, Wi-Fi, and RF circuits. In addition, dedicated display 104 can determine a historical trend of whether a user's glucose levels are trending down, remaining stable, or increasing. As shown in the example in FIG. 1, dedicated display 104 presents glucose readings over time so a user can easily monitor glucose levels, and displays an actual value of the current glucose level. In the example of FIG. 1, dedicated display 104 illustrates that the current glucose level is 94 mg/dL.

Display 106 can be any type of display associated with a personal computer, tablet, or smart phone that executes applications for displaying data relating to glucose levels. As a result, the display 106 includes hardware components typically associated with personal computing devices, including processor(s), memory, wireless connections, a USB port, and others.

Display 106 executes a plurality of applications 108~116 that relate to glucose monitoring, health information, exercise activity, controlling and monitoring insulin injections, eating habits, and others. In one embodiment, display 106 receives the same data that continuous glucose sensor unit 100 transmits to dedicated display 104. Display 106 includes a dedicated application 108 created by the manufacturer or an affiliate of the continuous glucose sensor unit 100. The dedicated application 108, display 106, and/or continuous glucose sensor unit 100 can be approved medical devices. For example, continuous glucose sensor unit 100, dedicated display 104, and dedicated application 108, alone or in combination, can be approved class III medical devices. The dedicated application 108 controls the distribution of medical data received from the continuous glucose sensor unit 100 to other third-party applications 110 and 114 executing on display 106 to preserve confidentiality and user preferences, as described in more detail below. Although not illustrated, dedicated application 108 can also be connected to and provide information to other third-party applications 112, 116, e.g., via applications the dedicated application 108 is in direct communication with, such as the approved third-party application 110 in the example shown in FIG. 1.

In the example embodiment shown in FIG. 1, the dedicated application 108 or an operating system executing on display 106 provides data relating to glucose levels to approved third-party application 110. For example, the dedicated application 108 receives glucose data from continuous glucose sensor unit 100, determines what set of data should be provided to an approved third-party application 110, and provides the data to the third-party application 110. A user, via the dedicated application 108, can configure what types of medical data to provide to the approved third-party application 110. In this manner, the third-party application 110 receives the same data set received by dedicated application 108 or a reduced set of data, of which may be provided as encrypted data. While dedicated application 108 has been described as controlling what data is provided to third-party application 110, an operating system executing on display 106 or other software program can also separate the data received from continuous glucose sensor unit 100 and provide it, as appropriate, to applications 108~116 with various restrictions.

The approved third-party application 110 can also share data with further third-party applications 114, 116. This provides a security risk because approved third-party application 110 obtains medical data from the continuous glucose sensor unit 100 or dedicated application 108, and provides it to additional applications 114, 116. The system of FIG. 1 can restrict applications 114, 116 from providing the medical data to additional applications, network storage sites, or other entities in an unauthorized manner. Users may want some third-party applications, such as approved third-party application 116, to access the medical data provided to application 110. As an example, dedicated application 108 provides glucose levels to an approved third-party application 110 that controls an insulin injection pump. In this example, a user wants the third-party application 110 to share glucose levels with third-party application 116 to provide effective feedback and allow more accurate control of insulin injections.

The dedicated application 108 can restrict other applications, such as one designed to calculate a distance that a user has run during exercise, from receiving the glucose data. The third-party application 110 and/or dedicated application 108 can still import exercise information to allow a user to easily track metabolic health information that impacts their glucose levels. Additional examples of restricting, encrypting, and otherwise protecting medical data provided to third-party applications 110~116 will be described below.

Figure 2A:
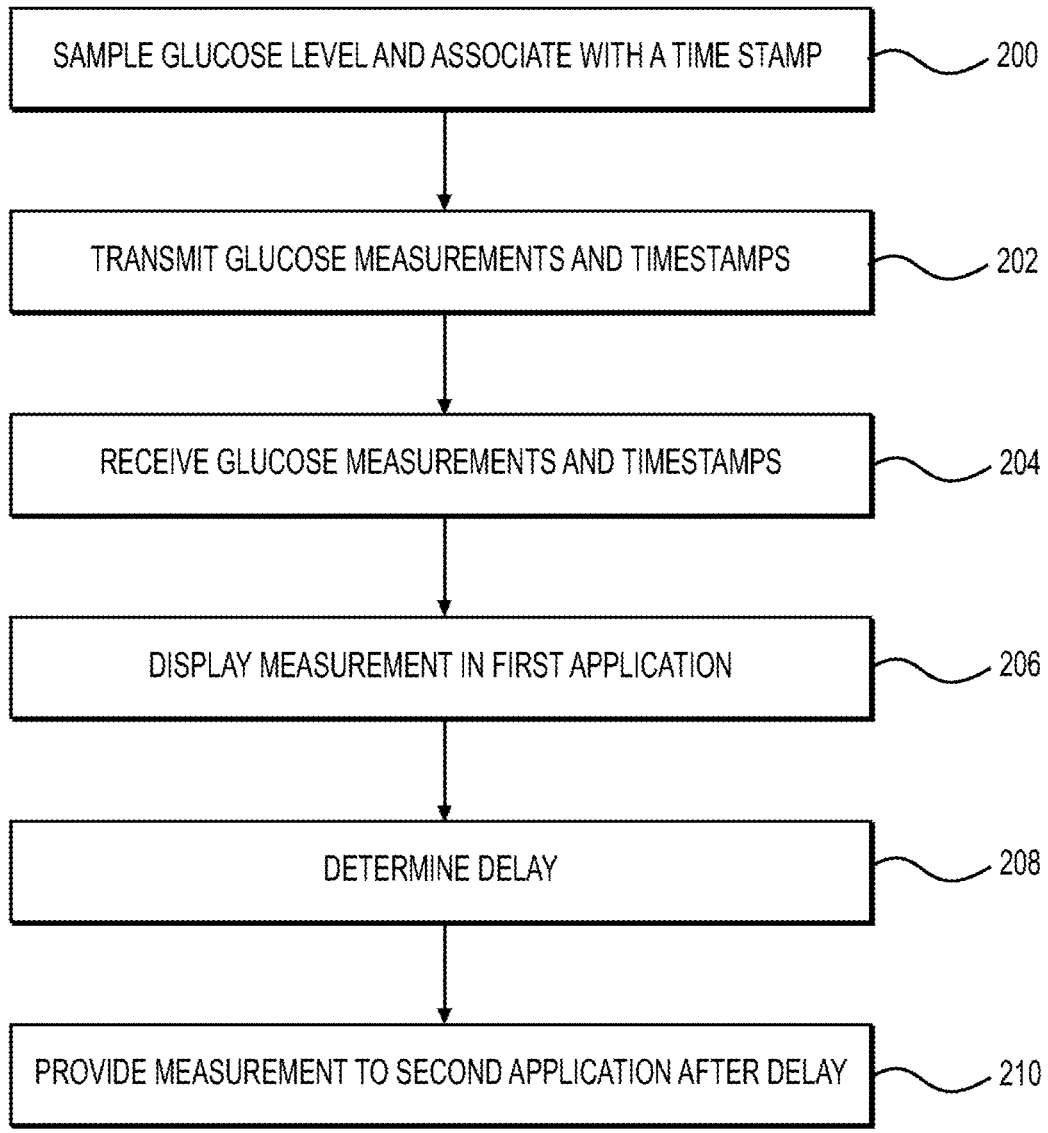
FIG. 2A illustrates an exemplary method for controlling the timing of providing glucose data to applications.

Reference will now turn to FIG. 2A, which illustrates an exemplary method for providing glucose data to applications including a dedicated application and third-party application(s). For example, the method can be implemented to control the accessibility of a user's sensitive health data, such as glucose levels, to third-party applications for protecting the safety and privacy of the user. For example, third-party applications may not be reliable or use the data relating to glucose levels correctly, even where calibration occurs at the sensor to provide calibrated values. In some cases, for example, the transmitter sends raw sensor data, and third-party applications do not have the correct formula for converting the raw sensor data to a glucose level. A conversion process can involve using the particular calibrations for a given individual and sensor, and without access to this information the third-party application creates inaccurate glucose levels from the raw sensor data. This can lead to potentially dangerous situations where a user does not receive a notification through a third-party application. In some embodiments, for example, the method of FIG. 2A can control the timing of redistributing medical data by delaying before providing the data relating to glucose values to third-party applications, e.g., which addresses both of the aforementioned situations. The delay prevents reliance on the accuracy of third-party applications in potentially hazardous health situations. Instead, the user will rely on dedicated display 104 or dedicated application 108 for recommendations based on real-time or non-delayed glucose levels.

At process 200, the continuous glucose sensor samples the glucose level and associates the sample with a timestamp. In one embodiment, a timestamp is the time when the continuous glucose sensor unit 100 generates a glucose data point, although in other embodiments a batch of samples that were measured within a time range can be given a timestamp.

At process 202, the transmitter sends the glucose measurements and associated timestamps to dedicated display 104 and/or display 106. The transmitter can send the measurements and timestamp continuously, at predefined intervals such as every five minutes, or on demand in response to a request from a user or device. In one embodiment, the continuous glucose sensor and transmitter can emerge from a low-power sleep state every five minutes, obtain a sample, and transmit the data before returning to the low-power sleep state. In other embodiments, the continuous glucose sensor takes multiple measurements and each measurement may be transmitted every five minutes, or a processor at continuous glucose sensor unit 100 may process the measurements to provide less than all of the measurements. As an example, a data processing unit on continuous glucose sensor unit 100 may average measurements taken over a period of time and transmit the average value and a timestamp associated with the first sample, the last sample, or the average sample time.

In one embodiment, the data transmitted from the continuous glucose sensor unit 100 also includes other data relating to monitoring a patient's glucose levels. For example, the continuous glucose sensor unit 100 transmits metadata including sensor calibration information, patient information, the type of sensor used to generate the measurements, system diagnostic information, rate of change information, a trend (e.g., glucose values rising, steady, or decreasing, or numerical values representing the rate of change), alarms or alert information, and/or a system status.

Examples of a system status include warm-up, which may be an interval after installing a new sensor when the sensor is warming up and calibrating, active, and offline.

The continuous glucose sensor unit 100 encrypts the data relating to glucose levels prior to transmission in some embodiments. Where Bluetooth communications are used, the encryption may be performed by a data processing unit on continuous glucose sensor unit 100 in addition to the standard encryption offered by Bluetooth devices. Further, the continuous glucose sensor unit 100 may transmit the data only to paired, authenticated devices in some embodiments. One-way or two-way authentication techniques may be used to ensure that continuous glucose sensor unit 100 only transmits data to authorized devices.

As one example, a transmitter identifier can be printed on continuous glucose sensor unit 100. A user may enter the transmitter identifier number in display 104 and display 106 as part of a pairing process that authenticates displays 104, 106 for communication with continuous glucose sensor unit 100. The continuous glucose sensor unit 100 and displays 104, 106 exchange private and public security keys during the pairing process or at the time of a user entering the transmitter identifier. By authenticating and pairing devices, the system can securely transmit data between continuous glucose sensor unit 100 and displays 104, 106 associated with that sensor. For example, multiple users with continuous glucose sensors 100 may be in a public area. In one embodiment, the displays 104, 106 can be paired and authenticated to their associated continuous glucose sensor unit 100 so that users do not receive data from other sensors within the wireless network range.

At process 204, dedicated display 104 and display 106 receive the data relating to glucose levels and associated timestamps from the continuous glucose sensor unit 100. Display 106 receives the glucose measurements and associated timestamps using, for example, dedicated application 108 or the operating system of display 106. The dedicated application 108 receives the data and distributes the data to other applications, such as third-party applications 114, 116, according to the set of controls for redistributing data described in more detail below. In some example implementations, dedicated application 108 may use encryption, provide less than all of the received data, and employ other techniques to maintain the confidentiality of a user's medical data.

At process 206, display 106 displays the data values in a first application, also referred to as the dedicated application 108 in the embodiment of FIG. 1. The first application 108 displays each of the received measurements on a graph so that a user can easily view their glucose levels over a period of time. For example, the sensor 100 may send a glucose level reading to each display 104 and 106 every five minutes.

The first application 108 may be executing in the background, so that displaying the glucose values does not actually occur until a user views the first application. The first application 108 receives the measurements and handles any processing required for display. In some embodiments where the continuous glucose sensor unit 100 transmits raw data values and the timestamps, for example, the first application 108 can convert the raw data values to a unit of measurement familiar to a user, such as mg/dL. The process of converting raw data values may also be done by, for example, the continuous glucose sensor unit 100 prior to transmission to the display 104 and/or display 106. The first application 108 executes such processes in the background and prepares the measurements for display, e.g., when the user selects the first application into the foreground.

The first application 108 may be part of an approved medical device. As a result, the first application 108 may, in some embodiments, process certain types of glucose measurements that would otherwise be restricted from other applications due to regulatory and/or safety concerns. Such certain types of glucose measurements may be one or more of real-time, actionable and predicted glucose measurements as opposed to retrospective glucose measurements. The first application 108 can use calibration values input by a user and the appropriate conversion formulas for a particular user and sensor in embodiments where the sensor unit 100 sends raw data values to the display 106. The first application 108 therefore maintains a level of accuracy required by approved medical devices.

In some embodiments, the first application 108 alerts a user when glucose levels fall below or rise above predefined levels. The first application 108 can escalate alerts based on the current time or activity of a user. For example, an alert that glucose levels have dropped to a low level during night hours may indicate that a user is asleep and a louder volume should be used for the alert. In some embodiments, a data processing unit executing on dedicated display 104 or display 106 samples data from an accelerometer. The first application 108 may determine that a user may be asleep based on the accelerometer data indicating the user is not physically active, resulting the in the first application escalating an alarm.

In addition, a user can set an alert to trigger a warning to a user when their glucose levels are trending in a particular direction or have changed by a certain amount within a given time period. The operating system or the dedicated application 108 tracks the glucose levels and issues the alarm or warning when appropriate. A user can therefore obtain accurate recommendations about managing glucose levels through the first application 108. For example, users may choose to eat additional food, exercise, control insulin injection, and/or perform other tasks based on the real-time display of glucose data provided by the first application.

At process 208, the first application 108 determines an amount of delay to employ before providing data relating to glucose levels to a third-party application. The amount of delay can be set by the manufacturer or the user. In some exemplary embodiments, the amount of delay can be, for example, between five minutes and three hours, although other values may also be chosen. The delay restricts third-party applications 110–116 from providing real-time recommendations to a user based on the restricted data for ensuring accurate health recommendations are made through the first application 108 based on current glucose levels.

The first application 108 can select the amount of delay based on which third-party application it provides the data to. For example, an approved third-party application 116 may have a shorter delay than other third-party applications, such as third-party application 112, which in the example of FIG. 1 has not been approved by the provider of the first application 108. In addition, the first application 108 can control the type of data to provide to each third-party application. In one embodiment, a third-party application may receive the same data as the dedicated application 108, or limited data such as with fewer data points, averaged data points, or an indication as to whether the glucose level is low, normal, or high without any specific data points. Additional examples of providing data to various applications will be provided below.

At process 210, the first application 108 provides the measurements and associated timestamps to third-party applications after the delay. A third-party application is also referred to as a second application. In one embodiment, the dedicated application 108 provides an indication of the amount of delay to the third-party application so that the third-party application can indicate to a user the time associated with the displayed measurements and/or the dely. The third-party application therefore displays delayed data and an indication of the amount of delay or a time when the continuous glucose sensor unit 100 obtained the measurement.

Process 210 can occur either by the first application 108 automatically providing the data to a second application after a delay, or by the second application requesting the data in accordance with some implementations. As an example of requesting the data, the second application may be turned off for a period of time and make a request to the first application 108 for any past data upon execution. In response, the first application 108 provides all of the data except the data that falls within the predetermined amount of delay. After startup, the second application continues to request data from the first application, or the first application automatically provides the data to the second application periodically. For example, the process 210 can be implemented using an application programming interface (API) of the dedicated application 108 that facilitates the transfer of the data to other applications, such as the third-party applications resident on the smart phone.

Implementations of the method of FIG. 2A allow a continuous glucose sensor unit 100 to transmit data to a display executing multiple applications. The first application 108 can use the real-time data for display, alerting a user, or other processing. The continuous glucose sensor unit 100 provides data indicating the glucose levels and timestamps indicating when the glucose levels were sampled. The first application 108 optionally displays the glucose levels and timestamps, and delays for a predetermined amount of time before providing the glucose levels and timestamps to a third-party or second application. The third-party or second application receives and uses delayed glucose levels. The third-party application can use the delayed glucose levels, for example, for display. In some embodiments, the third-party or second application receives a reduced set of data, or averaged data, as described below. In addition, in some embodiments a second application can receive some data in real-time and other data after a delay.

In some implementations of the exemplary method shown in FIG. 2A, the dedicated application 108 receives health data including a glucose measurement and associated timestamp or continuously generated glucose measurements with their respective associated timestamps at the process 104. At the process 208, the dedicated application 108 determines the amount of delay to employ before providing any of the received health data (e.g., the glucose measurement data) to other third-party applications, and determines that a time duration between a current time and the timestamp meets the determined amount of delay. The determined amount of delay can be inputted to the dedicated application, or be a predetermined default amount of delay. For example, the delay can be predetermined to be 3 hours or other time period recognized to render the data as retrospective data. In such implementations, at the process 210 the dedicated application 108 provides only retrospective glucose measurement(s) to the third-party application device only after the predetermined amount of delay. Similarly, in some implementations, at the process 210 the dedicated application 108 provides the glucose measurement(s) and/or any other health data determined to be delayed to the third-party application only after the determined amount of delay.

In such implementations, for example, the dedicated application 108 can be a medical device software application that configures the mobile computing device to receive and process medical data (e.g., such as the glucose measurement(s) provided by continuous glucose sensor unit 100), and the third-party application is not an approved medical device software application, i.e., not approved by a governmental regulatory institution authorized to regulate medical device technologies. Implementation of the exemplary method of FIG. 2A can therefore allow such unapproved third-party applications access to valuable medical data acquired, processed, and protected by a medical device software application, e.g., the dedicated application 108, in a manner that is in accordance with governmental regulations on medical devices and/or medical data as well as valuable to the end user (e.g., the patient user and his/her network of caregivers, remote monitors, etc.) to obtain and view such data on third-party applications that may integrate and enrich the medical data. The third-party applications can obtain, process and output the medical data in any way the third-party application is capable. In an illustrative example, the third-party application can include meal tracking functionality that can be integrated with the glucose measurement data provided by the dedicated application 108, obtained in accordance with the exemplary method of FIG. 2A. The third-party application can integrate the glucose data with the meal information to provide valuable insights to the user, e.g., such as correlating meals with fluctuations of the user's glucose levels.

In some embodiments, for example, the exemplary method of FIG. 2A can include a process to create subsets of data from the received health data, in which a first subset of data and a second subset of data are generated (e.g., by dividing the received health data into the subsets, and/or by producing at least some new or modified data based on the received health data) according to a predetermined criteria. The exemplary method of FIG. 2A can include a process to control which subsets of data are to be provided to the third-party application(s) after determining the delay the determined subsets that are to be provided.

Figure 2B:
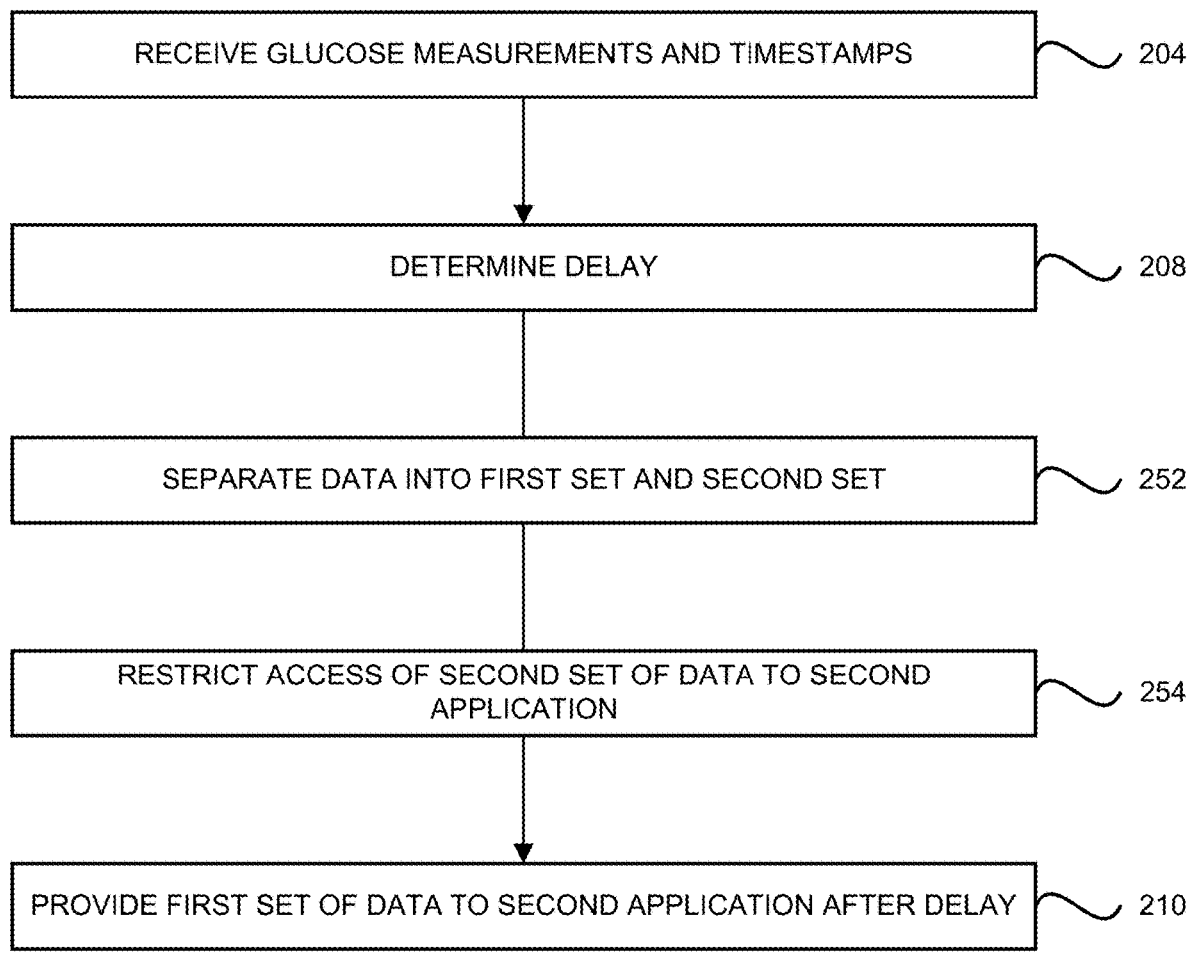
FIG. 2B illustrates an exemplary method for controlling the timing and categorization of glucose data for distribution to applications.

FIG. 2B illustrates an exemplary method for controlling the timing and categorization of glucose data for distribution to applications. The exemplary method of FIG. 2B is described with reference to the system of FIG. 1 and the methods of FIG. 2A and FIG. 5 for illustrative purposes, and may be used with other systems and/or and processes than those described in the exemplary embodiments of FIG. 2B. As illustrated in FIG. 2B, the exemplary method includes the process 204, in which the dedicated display 104 and/or the display 106 receive the data relating to glucose levels and associated timestamps from the continuous glucose sensor unit 100. The received data can include continuously generated glucose level measurements and their associated timestamps. For example, the display 106, e.g., mobile computing device such as a smart phone, receives the glucose measurements and associated timestamps using the dedicated application 108 or the operating system of display 106. The exemplary method of FIG. 2B includes a process 252, in which the first application 108 separates the received data into a first set of data and a second set of data. In some implementations of the process 252, the first application divides the continuously generated glucose measurements into the first and second sets of data based on a predetermined criteria, e.g., such as a category or type of the data (e.g., which may be identified by a data field or metadata of the data), a timestamp of the data, a size of the data, a source of the data, or other factor associated with the received data. In some implementations of the exemplary method, the received data includes additional health or medical data, and the process 252 includes the first application 108 creating a set of data relating to the continuously generated glucose measurements from which the first and second sets of data will be formed. The exemplary method of FIG. 2B includes a process 254, in which the first application 108 restricts access to the second set of data to a second application, e.g., one or more of third-party applications 110~116. The exemplary method of FIG. 2B includes the process 208, in which the first application 108 determines an amount of delay to employ before providing data to a third-party application, e.g., which can be set by the manufacturer and/or by the user, such as five minutes, three hours, or other time delay value. In some exemplary embodiments of the method of FIG. 2B, the process 208 can be implemented prior to the processes 252; and in other exemplary embodiments, the process 208 can be implemented after the process 252, e.g., including after the process 254. The delay restricts the third-party applications 110~116 from providing real-time recommendations to a user based on the restricted data for ensuring accurate health recommendations are made through the first application 108 based on current glucose levels. The exemplary method of FIG. 2B includes the process 210, in which the first application 108 provides the first set of data to the second application (e.g., the one or more of the third-party applications) after the delay.

Figure 3:
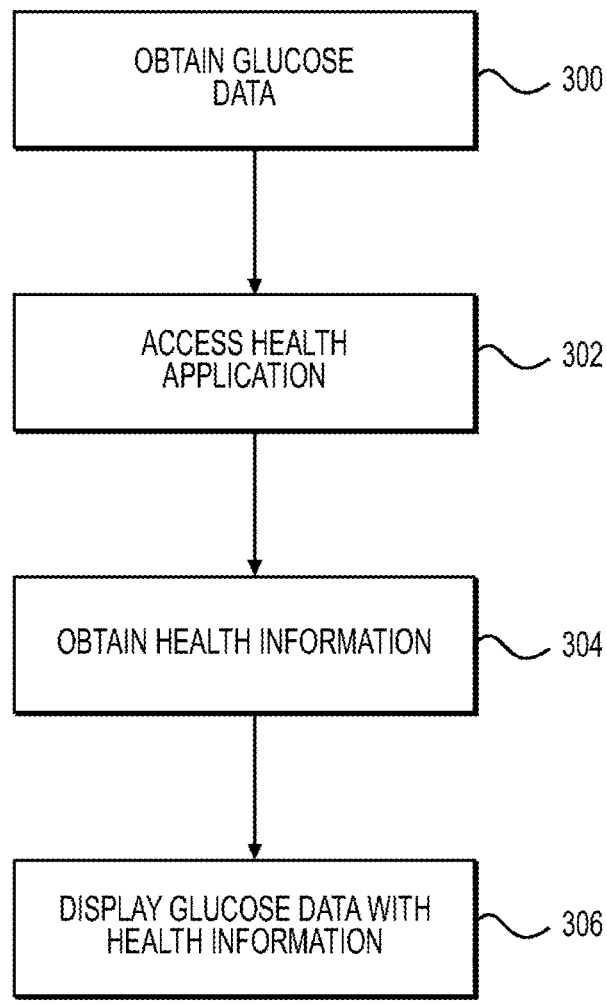
FIG. 3 illustrates an exemplary method for integrating glucose levels with health information.

FIG. 3 illustrates an exemplary method for integrating glucose levels with health information. The method of FIG. 3, and the other methods described herein, are described with reference to the system of FIG. 1 for illustrative purposes. The disclosed methods may be used with other systems and different components of the system than described in the exemplary embodiments. As illustrated in FIG. 1, third-party application 110 can provide a centralized way for a user to access health information. Display 106 can execute a plurality of applications relating to health information. Some examples include applications that track sleeping patterns, monitor food and caloric intake, track exercise, measure calories burned, monitor blood pressure, control and record insulin injections, monitor heart rate, monitor consumption of supplements and medicines, and others. These third-party applications, such as the third-party applications 114, 116, provide information to an approved third-party application 110 that stores health-related information for a user. Many different types of health information can impact glucose levels and an individual's health, in general, be it diabetes related or otherwise. Therefore, the method of FIG. 3 obtains health information from a third-party application that serves as a health information repository and distribution interface for other application to deposit and access health information. The dedicated application can integrate health information from the third-party application for display with glucose levels so that a user can track correlations between health information and glucose levels.

At process 300, dedicated application 108 obtains glucose data as described previously. Next, at process 302, the dedicated application 108 accesses the health application that serves as a repository for health information (also referred to herein as a distribution application). For example, the health application can include the approved third-party application 110. In some implementations, the third-party application 110 may serve as a repository that receives and stores health information from a third-party application 114 that tracks exercise activity and from an approved third-party application 116 that controls insulin administration.

In some implementations of the process 302, the dedicated application 108 can access the health application through standardized application program interfaces. The dedicated application 108 can check the health application for any new data at the occurrence of an event. The event can be, for example, an amount of time, launching or opening of an application, detecting that a glucose level crosses a threshold value, and other events. As specific examples, the dedicated application accesses the health application to check for updated data periodically (e.g., every fifteen minutes), in response to detecting that glucose levels have risen or fallen to predefined levels, in response to detecting a rate of change in glucose levels, on demand at the request from a user, when the dedicated application 108 is executed, a predetermined pattern of one or more monitored health characteristics (e.g., pattern indicating the person being monitored ate a meal, administered insulin, and is exercising or sleeping) and the like. In addition, the third-party application 110 or operating system executing on the display 106 can push information to the dedicated application 108 in response to the occurrence of any of the previously described events.

As one example, continuous glucose monitor 100 sends dedicated application 108 glucose measurements and associated timestamps in the process 300. In the process 302, the dedicated application 108 accesses the health application 110 upon detecting that glucose levels have dropped by a defined amount, such as by dropping 50 mg/dL within a thirty-minute interval. For example, the rapid drop in glucose level signals can indicate that a user is exercising, which indicates the health application may have received or be receiving exercise information from another application that tracks exercise activity. In response to detecting the change in glucose levels, the dedicated application 108 obtains the health information from the health application 110 in a process 304, described below.

At process 304, the dedicated application 108 obtains health information from the health application through standardized interfaces. The health application provides the health information to the dedicated application 108 automatically in response to an event, as described previously, or in response to a request from the dedicated application 108. The health application can include standardized application program interfaces that provide a list of acceptable commands and the format for any responses. For example, the dedicated application 108 can send a command such as: retrieve exercise activity, and receive a response with two variables—one indicating the type of activity (e.g., running, lifting weights, walking, swimming, etc.) and the duration of the activity. While an example has been provided, it will be appreciated that other application program interfaces can be used to exchange information between the dedicated application 108 and the health application.

This health information may include, for example, an indication that a user has taken a particular medication, the dosage, and the time the medication was taken; nutrition information such as calories and sugars consumed; body measurements such as a user's height, weight, blood pressure, and heart rate; insulin information indicating the time and dosage of insulin that a user injected; and other types of health information.

As another illustrative example, dedicated application 108 detects a given rate of change in glucose levels and prompts a user for health-related information. The user enters the health-related information directly into dedicated application 108 or the health application, such as approved third-party application 110. For example, dedicated application 108 can detect a sudden rise in glucose levels and prompt a user to enter meal information, or detect a drop in glucose levels and prompt a user to enter exercise activity. Moreover, prompts from other distributed systems, such as a cloud monitoring glucose values of a user, or from another application that monitors glucose values may trigger a prompt to enter or access health information.

Dedicated application 108 can control and configure the types of health information to obtain from the health application. As an example, a user may be comfortable with the dedicated application 108 accessing, for example, exercise and nutritional information, but not a record of medicines. In one embodiment, before providing any health information to a user, the dedicated application 108 prompts a user to confirm that the dedicated application 108 can access the desired health information from the health application. The user provides permission for a category of health information or only for specific items of health information. For example, one user may want to allow access to all health information relating to medicines taken, while another user may want to limit medicine consumption to only insulin. The dedicated application 108 stores data and creates controls to obtain the authorized information. In addition, the dedicated application 108 allows a user to revoke permission at any time to prevent the dedicated application 108 from accessing some or all of the health information stored by a health application.

The dedicated application may also obtain health information from other applications or from hardware on the dedicated display 104 or display 106. For example, display 106 may include an accelerometer. Dedicated application 108 may obtain health information in the form of accelerometer values that indicate exercise activity, by directly accessing the accelerometer values, accessing an operating system on display 106, or through any other application.

Figure 4:
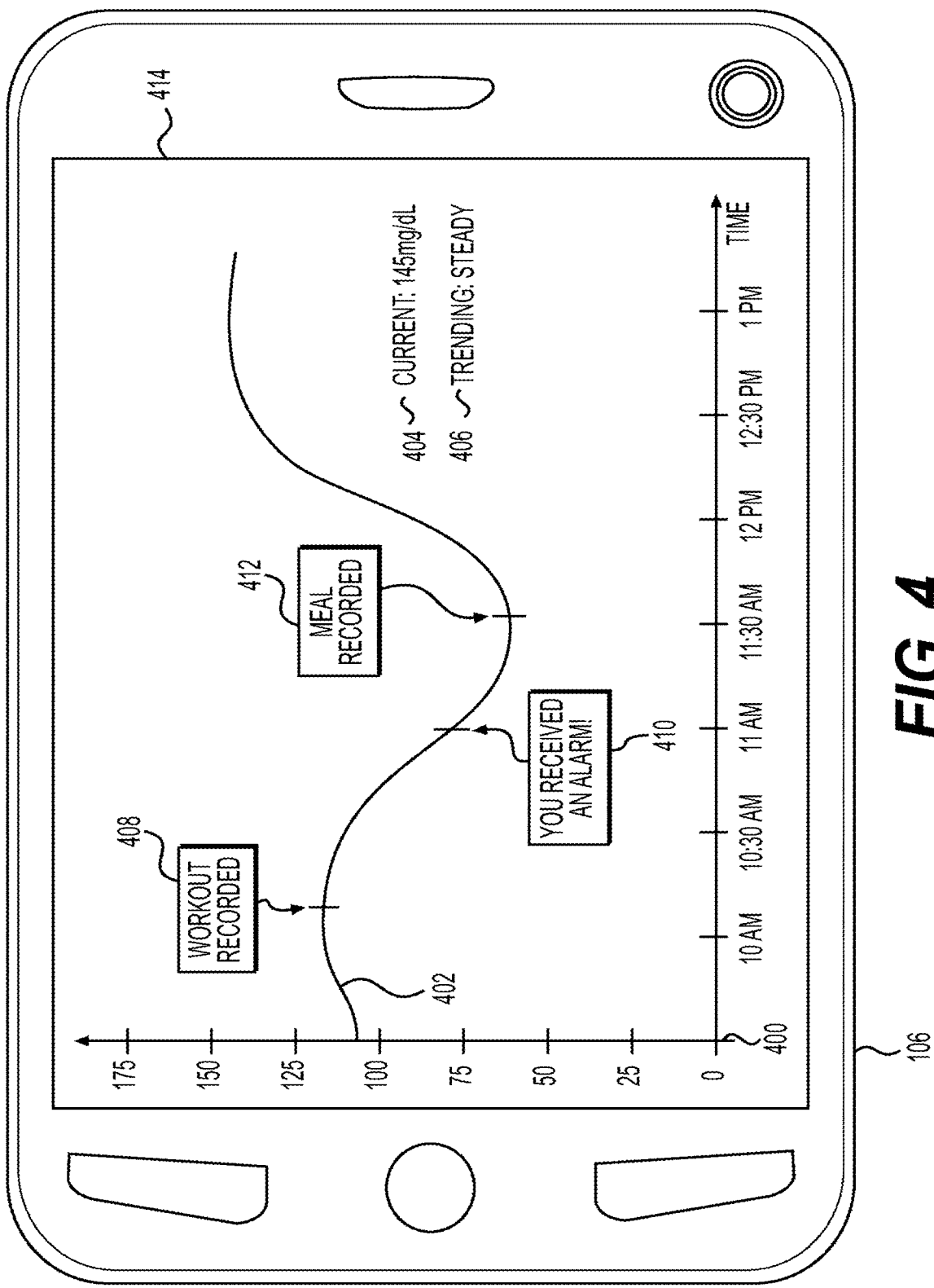
FIG. 4 illustrates an exemplary user interface for monitoring glucose levels with integrated health information.

At process 306, the dedicated application may display the glucose data along with health information obtained from health application 110. An example display is shown in FIG. 4, although other display configurations may also be used. FIG. 4 illustrates a chart with glucose levels along the y axis and time along the x axis. The curve line 402 illustrates continuous glucose levels based on data received from the continuous glucose sensor.

As illustrated in FIG. 4, a user's continuous glucose levels 402 may be illustrated trending over a period of time beginning at 9:30 am. A first example of health information is shown at 408, where the display illustrates an indication that a workout was recorded shortly before 10:30 am. A third-party application can track exercise activity and record the start of a workout. The health application obtains a record of the workout from the third-party application while the workout is in progress or upon completion of the workout in an implementation of the process 304, for example. In this example, dedicated application 108 may access the health information at 10:30 am and receive an indication that a workout was recorded at 10:25 am. Although not illustrated, a user may select the workout recorded icon 408 to view more information about the workout, such as the duration of the workout, calories consumed, and any other information that the third-party application provided to the health application that the dedicated application also has authorization to access. As shown along continuous glucose levels 402, shortly after the workout, glucose levels trended down sharply. The integrated display therefore provides a convenient way for a user to correlate glucose levels with particular activities and health information.

The display also shows an alarm that glucose levels dropped below a defined amount or trended down at a defined rate, as illustrated at 410. Subsequently, at 412, the dedicated application 108 displays integrated health information indicating that a meal was recorded in dedicated application 108, the health application, or another application. In one embodiment, the dedicated application 108 accesses the health application again at 11:45 am and determines that new health information in the form of a recorded meal was entered into the health application. The user may select the meal recorded icon 412 and receive any additional information relating to the meal, such as the amount of calories and sugars consumed.

In one embodiment, the dedicated application 108 accesses health information automatically in the example shown in FIG. 4. As illustrated, the glucose levels were dropping from roughly 10 AM until 11:30 AM when the levels stabilized and then began to rise. The dedicated application 108 detects the change from a steadily decreasing glucose level to a constant or rising glucose level and uses the change as a trigger for accessing the health information from health application 110. The change indicates a user was engaged in other activity that impact glucose levels. In this example, that other activity is a meal that a user consumed, although it could also be, for example, a user administering glucagon. The process of automatically accessing the health application may occur instead of, or in addition to, other techniques such as periodic access.

The user interface 414 can also include additional information for a user to track their glucose levels and health information. For example, the current glucose level can be shown at 404 and the current trend in glucose levels can be shown at 406. The current trending levels can be over a period of time, such as the most recent five, ten, or thirty minutes, or another interval. The trend can be shown also as an arrow pointed down to indicate a dropping glucose level, horizontal to indicate a steady glucose level, or up to indicate a rising glucose level. In addition, although not illustrated, the display can present other information, such as a red light to indicate a caution due to glucose levels being out of a desirable range or a green light to indicate that glucose levels are acceptable.

Although integration of health information with glucose levels has been described as importing health information into the dedicated application 108, glucose levels may also be integrated with health information in a health information application, such as any of third-party applications 110~116. For example, a food application allows users to take a picture of their food and determines from the picture the type of food and nutritional values. The food application obtains glucose values from the dedicated application 108 and overlays a chart, similar to the chart shown in FIG. 4, on an image of the food. As a result, a user can easily associate changes in glucose values with particular types of food consumed based on the stored food images. In other applications, the integration of glucose levels can allow applications to better identify patients in need of attention, develop custom analytics for patient care, improve diabetes clinical outcomes, and monitor patient risk between office visits to a doctor.

Figure 5:
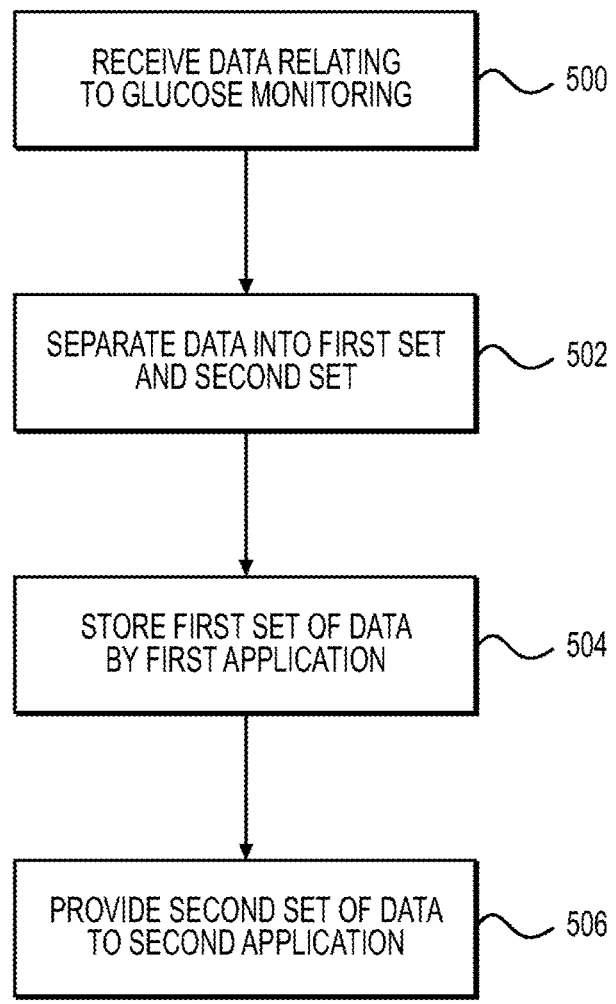
FIG. 5 illustrates an exemplary method for separating data relating to glucose levels for different applications.

FIG. 5 illustrates an exemplary method for separating data relating to glucose levels for different applications. Continuous glucose sensor unit 100 transmits sensitive medical data to displays 104 and 106. The amount and type of data provided to various applications can be restricted to ensure authorized uses of the medical data. In one embodiment, the determination as to the amount and type of data to distribute can be based on the level of security offered by each application and/or preferences of a user. The method of FIG. 5 allows the full set of medical data, including actual glucose levels, timestamps, and other data, to be separated into different sets depending on the application to receive the medical data. This method allows sensitive medical data to be protected after receipt from the continuous glucose sensor unit 100 and upon further distribution to display devices and applications executing on the display devices. Unapproved applications often suffer security flaws that are unacceptable for sensitive medical data. For example, an application may redistribute sensitive medical information without any restrictions on redistribution, leading to a cascading effect that compromises a patient's privacy, or in extreme cases could risk the patient's health. As another example, the applications may not use encryption or other forms of security, making them vulnerable to being compromised. Accordingly, the method of FIG. 5 separates data relating to glucose levels to control and limit the types of data provided to various applications.

At process 500, the first application, such as dedicated application 108, receives data relating to glucose levels from the continuous glucose sensor unit 100. This data includes, for example, a plurality of glucose level measurements and associated timestamps indicating when the measurements were taken, as well as metadata including calibration information, patient information, the type of sensor used to generate the measurements, system diagnostic information, rate of change information, a trend (e.g., glucose values rising, steady, or decreasing), alarms or alert information, and/or a system status. The data may also include personal identifying information for a user, calibration data for the continuous glucose sensor unit 100, system diagnostic information, and/or other private health information about a patient. The data can also be generated by a user via user input into the dedicated application 108 or another application 110~116, or by the operating system or dedicated application 108 pulling data from a server. In some implementations, the dedicated application 108 obtains the data from the continuous glucose sensor unit 100 as described previously.

At process 502, the first application 108 separates that data into a first set and a second set according to a predetermined criteria, e.g., established controls. The established controls include, for example, rules for restricting access to a complete set of data for third-party applications, which may be based on user preferences or on default controls. For example, a user may establish a control so that the first application 108 provides data to an approved third-party application 110, also referred to as a second application. The first application 108 can include controls based on user input, or default settings previously determined based on user preferences, to establish which types of data will be provided into a second set of data for the third-party application. Also for example, the first application 108 can include default controls independent of the user's preferences to establish the rules for restricting access to particular data for third-party applications, e.g., to prevent access to data that could risk the patient's health. Examples of the data separated into the second set of data for the third-party application can include only averaged glucose values over defined intervals (e.g., such as fifteen minutes rather than all of sampled the glucose values), and/or generalized indications of glucose levels instead of the actual measurement values, in which exemplary indications include low, normal, or high, where the bounds of what levels constitute low, normal or high are predefined by the system or user. In some implementations where the data is determined to be appropriate for both the first set of data and the second set of data based on the predetermined criteria, then the second set of data can include the same data as the first set of data.

In one embodiment, the process 502 includes using metadata associated with the types of data to separate the data into subsets. For example, the metadata relating to the calibration of the continuous glucose sensor, system diagnostic information, patient identifying information, and/or a system status may be excluded from the second set of data. Another example of data associated with glucose values is an estimated range of error. Continuous glucose sensor unit 100, dedicated display 104, or display 106 using the first application 108 may associate an estimate range of error with the measurements taken by the sensor. The estimated range of error may, in some embodiments, be included in the first set of data, the second set of data, or both.

The first application 108 may separate the data in a variety of manners, including logically in software or physically in memory. For example, the first application 108 can cause a device, such as the sensor unit 100, display 104, display 106 or another computing device in secure communication with the device executing the first application 108, to store a duplicate copy of data in memory for the first set of data and the second set of data, store records into a logical database of which data belongs in each set, or store a single set of data with restricted values being provided only to the first application but not the second application. In other embodiments, continuous glucose sensor unit 100 can separate the data into two sets prior to transmission, or an operating system of the device executing the first application 108 (e.g., display 106) can perform the separation. In addition, although described as separating the data to provide a single or reduced set of data to particular applications, the first application 108 can also restrict other applications (e.g., third-party applications or additional applications as part of a suite of dedicated applications) by granting the other applications access to specific types of data based on predefined rules. The predefined rules are set by the manufacturer and/or a user of the system in some implementations. In such cases, the access-granted types of data may be retrieved from the other applications in communication with the first application 108, and not necessarily be provided to the other applications as described later in process 506.

Figure 6A:
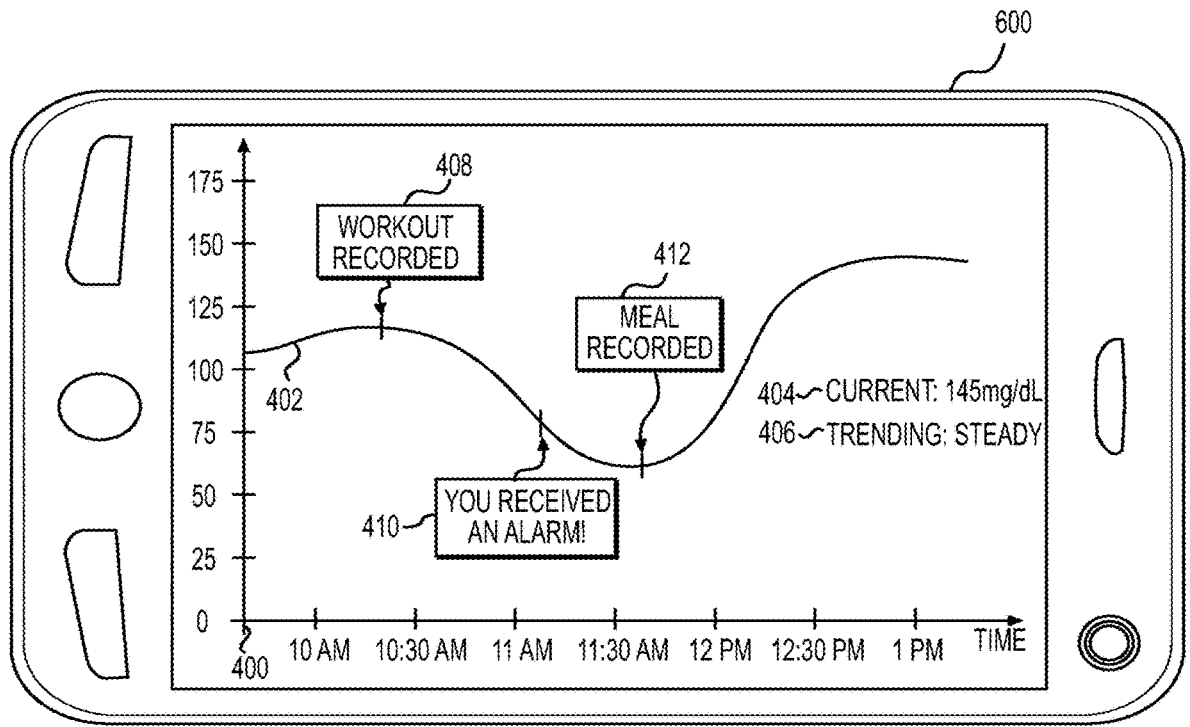
FIGS. 6A and 6B illustrate exemplary user interfaces displaying separated data relating to glucose levels.

At process 504, the first application 108 stores the first set of data. For example, the first application 108 can store the first set of data on the display 104, display 106, sensor unit 100, and/or another computing device in secure communication with the device executing the first application 108. In one embodiment, the first set of data includes the complete set of data received from continuous glucose sensor unit 100. The first application 108 stores the first set of data in memory of the display 106 and makes it available for display, such as shown in the exemplary user interfaces of FIGS. 4 and 6A. With reference to FIG. 6A, a user interface 600 displays a first set of data including a plurality of continuous glucose levels shown over a period of time to aid a user in monitoring glucose levels.

Figure 6B:
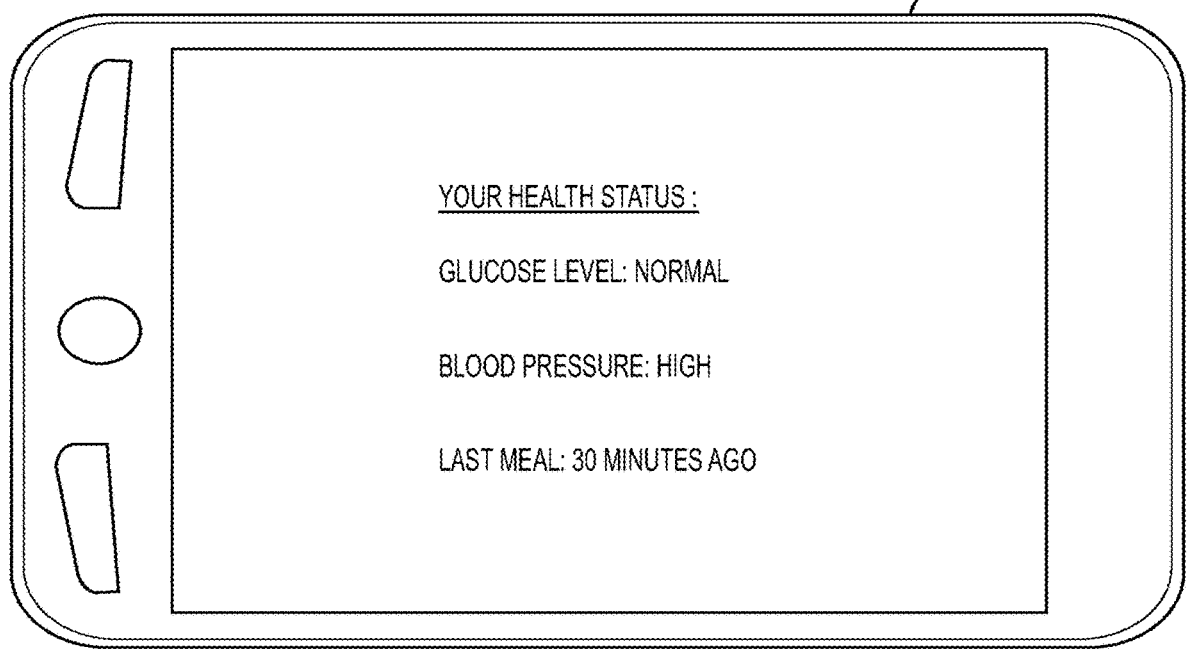

At process 506, the first application 108 or an operating system executing on display 106 provides the second set of data to a second application. The second set of data includes a reduced set of a data appropriate for use by a third-party application. For example, FIG. 6B illustrates a user interface 602 with a third-party application displaying a second set of data that indicates a health status with a glucose level of normal. In one embodiment, the third-party application also displays other health information obtained from dedicated application 108 or another third-party application, such as the user's blood pressure and the last time the user consumed a meal.

The first application 108 can provide the second set of data to the second application by pushing the data to the second application, transmitting a notification to the second application informing the second application to request the data, or making the data available for access in response to a request from the second application. The second set of data may be provided periodically, on demand, or in response to a particular event. For example, when a user launches the second application, the second application requests any updated data, including the second set of data, since the second application was last launched.

While two sets of data have been described, the system can also create additional sets for each application. A user may choose to provide data relating to glucose levels to a plurality of applications, and each application may receive a set of data based on the permissions granted to the application. In this embodiment, the method of FIG. 5 may be executed a plurality of times to create additional data sets.

Figure 7:
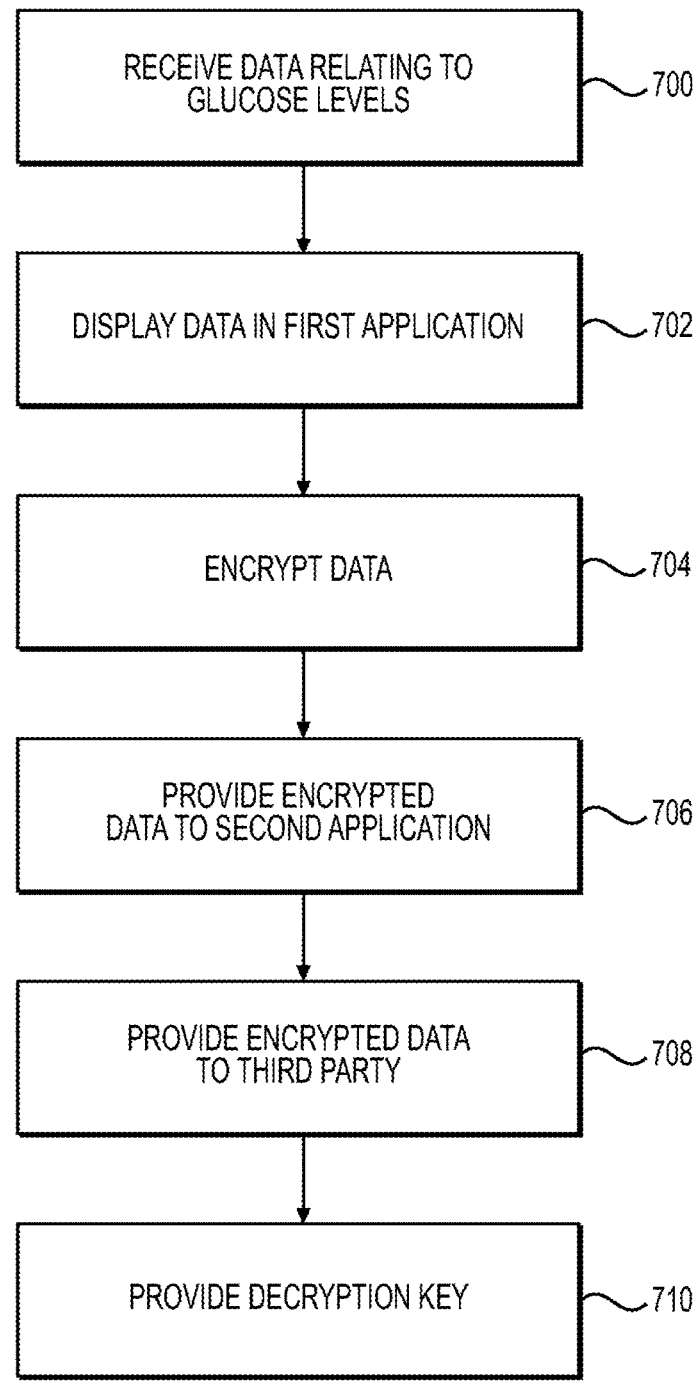
FIG. 7 illustrates an exemplary method for encrypting data relating to glucose levels.

FIG. 7 illustrates an exemplary method for controlling redistribution of medical data by encrypting data relating to glucose levels. One way to control access to medical data is by encrypting the data prior to transmission from the continuous glucose sensor or prior to distribution of the medical data, or subsets of it, to other applications. Third-party applications can share their data with other applications, which can also distribute data to servers, the Internet, and other devices. As a result, when the transmitter or dedicated application provides data relating to glucose levels to other applications, there is a need to control the manner in which the other applications can access and redistribute the data. In the example of FIG. 7, the dedicated application 108 or sensor unit 100 can encrypt the data before providing the data relating to glucose levels to other applications, providing enhanced security and a way to prevent unauthorized third-parties from unpermitted use of the data. In particular, unauthorized third-parties will not have a key to decrypt the data.

FIG. 7 relates to encrypting data before providing it to third-party applications. A key to decrypt the data may be provided to authorized third-party applications. As a result, with reference to FIG. 1, approved third-party application 116 can access glucose data through approved third-party application 110, but approved third-party application 110 or other third-party applications, such as 114, can be prevented from accessing the data. In this exemplary embodiment, approved third-party application 110 may act as a pass-through that provides information to other applications.

The decryption key can be provided to the approved third-parties in a variety of ways. For example, in some implementations, the approved third-party application 116 receives the key to decrypt the data directly from dedicated application 108, through third-party application 110, or from another source.

At process 700, display 106 and a first application, such as dedicated application 108, receive data relating to glucose levels from continuous glucose sensor unit 100 as previously described. The first application 108 stores and displays the data at process 702 as previously described. For example, the first application displays a continuous level of glucose levels over a period of time, a current glucose level, and trending glucose levels.

At process 704, the first application 108 or an operating system executing on display 106 encrypts the glucose data. The encrypted data may include all of the data received from continuous glucose sensor unit 100, or a subset of the received data as described previously with reference to FIGS. 5, 6A, and 6B, and also other data generated at dedicated application 108. Encryption may be performed using a variety of different techniques, including public/private key encryption, among others. The type and amount of data that the first application 108 or operating system encrypt can vary depending on the application to receive the data. For example, one receiving application may receive all data in real-time, another receiving application may receive data after a first delay, such as fifteen minutes, and another application may receive data after a longer delay, such as three hours. Also, for example, the first application 108 may encrypt all of the data using one encryption technique having a first encryption key and a separated subset of the data using another encryption technique having another encryption key, in which the data sets and corresponding decryption keys may be received by only their intended applications. In addition, encryption software on third-party applications can decrypt only certain types of data and/or decrypt data only after a predetermined amount of delay. The first application 108 or operating system can provide the same or different data to each application, so that certain types of data relating to glucose levels can be restricted from any given application. In some embodiments, the first application 108 or operating system provides encrypted data in real-time but provides the key after a predetermined amount of delay, preventing that the receiving application from decrypting the data until an authorized time.

At process 706, the first application 108 or operating system may provide the encrypted data to a second application, such as approved third-party health application 110. In some embodiments, the data provided to the second application includes a key to decrypt the information, whereas, in some embodiments, no key is provided.

In the examples of providing the data to a second application without a decryption key, the second application provides the data to another application at process 708 and acts as a pass-through entity by providing the encrypted data without its own independent ability to decrypt it. With reference to FIG. 1, an example is shown where third-party application 110 provides encrypted data to approved third-party application 116. Although described as a third-party or a third-party application, it will be appreciated that the application 110 or 116 need not be from a third-party.

At process 710, the third-party (e.g., the third-party application 116 in the example above) that received the encrypted data from the second application (e.g., the third-party health application 110 in the example above) may receive a decryption key. The decryption key may be provided directly to the third-party from the first application 108, from an operating system executing on display 106, through the third-party application 110, from another application, or from another source such as a server over the Internet. In some embodiments, the first application 108 controls which third parties receive the decryption key to control future use of data, such as through a configuration by the user.

The encryption techniques may change periodically or on demand so that a new decryption key is required to access the data. Accordingly, a user can request that data be encrypted and a key provided for only a defined period of time. As an example, a doctor may use a third-party application to control insulin injections. The dedicated application 108 or operating system executing on display 106 encrypts and transmits glucose data from the continuous glucose sensor unit 100 through approved third-party application 110 to the application used by the user's doctor's office. The doctor's application allows medical workers to monitor glucose levels and make recommendations to a user. However, if a user switches doctors, the first application can revoke permissions to receive or decrypt the data by not allowing the approved third-party application 110 to provide the data to the doctor's application and by changing the encryption key.

Figure 8:
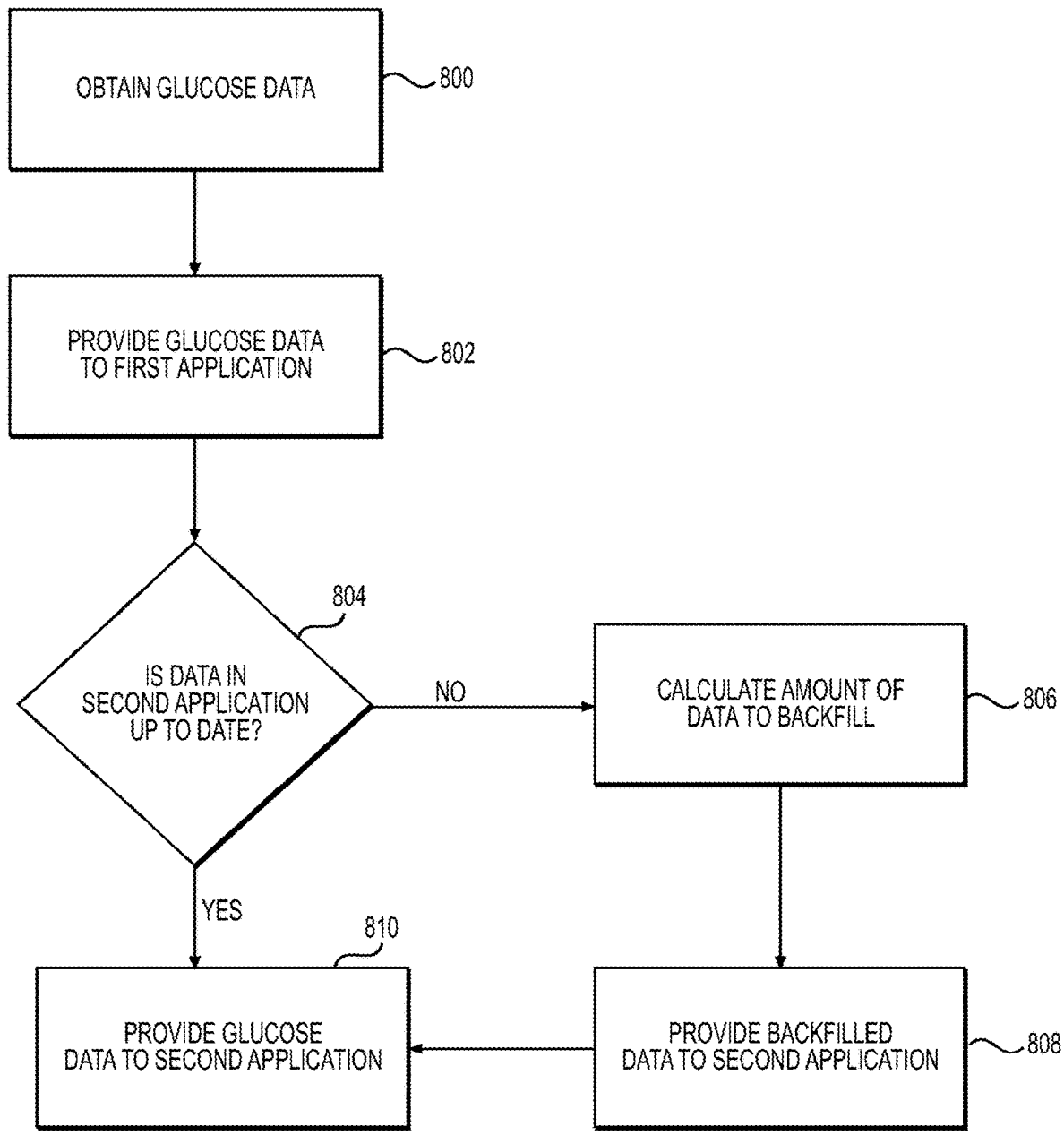
FIG. 8 illustrates an exemplary method for providing data to applications and monitoring whether the data has been updated.

FIG. 8 illustrates an exemplary method for providing data to applications and monitoring whether the data is up to date. One problem that occurs when providing data to multiple displays and multiple applications executing on a display is ensuring that each application or display includes up-to date data. For example, a user can turn off an application, so it will not receive data from the first application. In other embodiments, an application can be inactive, a display could be turned off or out of wireless transmission range, or applications may receive data in response to a user request. If an application does not receive glucose data for a period of time, the application will not be up to date. The method of FIG. 8 therefore allows the old data to be backfilled into an application to bring the application up to date. Up to date can mean that the application has all data available to it. For example, in the situation where the application receives data after a predetermined delay, as previously described, up to date can mean the application has all available data up to the predetermined delay.

At processes 800 and 802 in FIG. 8, display 106 receives glucose data and provides the data to a first application as previously described. At process 804, the first application 108 or operating system executing on the display 106, or in some implementations involving the second application, determines whether the glucose data in the second application is up to date. In one embodiment, the first application 108 keeps a record of when it provided glucose data to the second application. The second application confirms receipt of the glucose data to allow accurate record keeping of the most-recent data provided to and received by the second application. In other embodiments, the second application sends the first application an indication of the time associated with its most recent glucose value, e.g., which may be periodically, intermittently or in response to a query or request by the first application 108 or the operating system executing on the display 106. In either exemplary embodiment, a determination is made as to whether the second application is up to date and includes recent glucose levels from continuous glucose sensor unit 100.

The second application may be considered up to date when it has received data up to any predetermined amount of delay, e.g., as described with reference to FIG. 2A. When the second application is up to date, the first application 108 provides any new glucose data at process 810. However, if the second application is not up to date, the first application 108 calculates an amount of data to backfill at process 806.

In one embodiment, the first application 108 determines the amount of backfills data based on a defined range of time, e.g., which excludes data beyond a given age (outside the range of time). For example, the first application 108 stores continuous glucose data spanning a period of days, weeks, or even months. If the second application has been turned off for an extended period of time, or is being installed and executed for the first time, the first application 108 can backfill data within the last six hours. The first application 108 can also use other durations, as six hours is provided only as an example. Also, in some implementations, the user may request that additional data be backfilled into the second application beyond any default range. The user may also input a start and end date during which to backfill data into the second application.

The process 806 of calculating the amount of data to backfill can occur automatically, in response to a request by a user, or after a user has been prompted about whether to backfill and answered affirmatively. After the process 806, at process 808, the first application 108 provides the backfilled data to the second application, e.g., which may be implemented using application program interfaces. Once the first application 108 has backfilled the selected range of data into the second application, the first application 108 provides any new glucose data to the second application at process 810. Alternatively, the first application 108 can first provide current glucose data, and then backfill prior data.

Figure 9A:
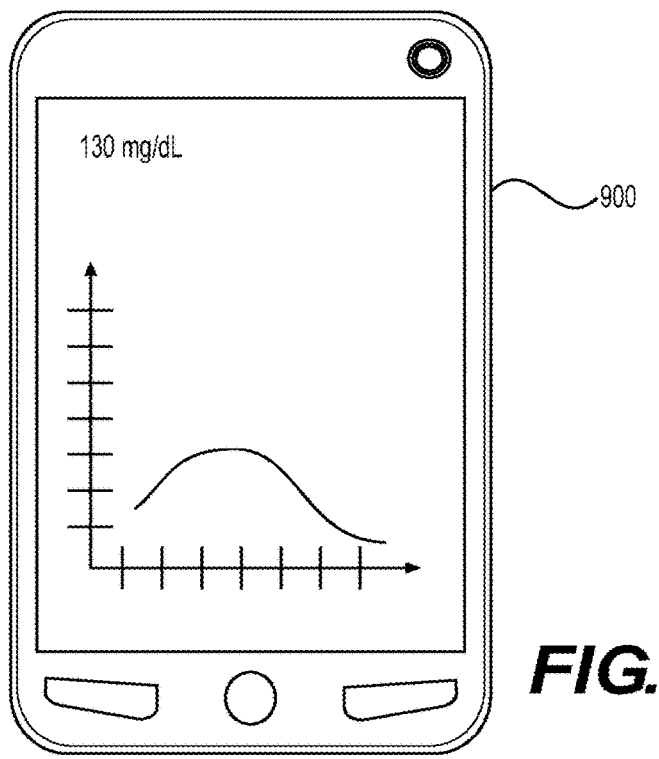
FIGS. 9A and 9B illustrate exemplary user interfaces for displaying data relating to glucose levels and an indication of whether data was backfilled.
Figure 9B:
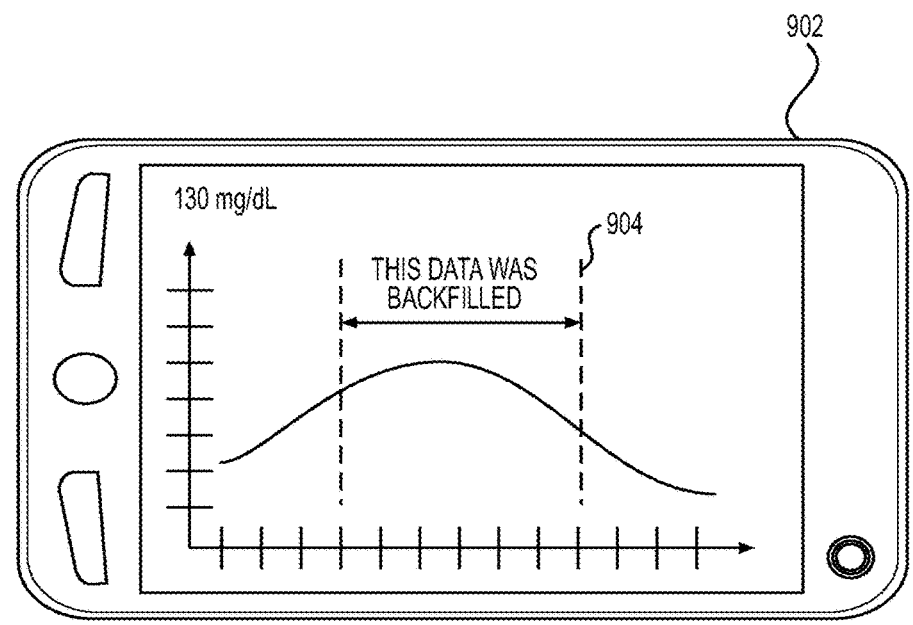

FIGS. 9A and 9B illustrate exemplary user interfaces for displaying data relating to glucose levels and an indication of whether data was backfilled. In FIG. 9A, a user interface 900 provided by the first or second application may include a chart illustrating glucose levels over a period of time as described in embodiments described herein when in a portrait mode. However, when a user rotates display 106 to a landscape mode, the user interface 902 illustrates an indication 904 that data in a given range was backfilled.

The display can also indicate that data has been backfilled using other techniques. For example, a line illustrating sampled glucose levels may use a different color or different pattern during intervals with backfilled data. A user who uses the second application for alerts when glucose values fall below a defined level may wonder why an alarm was not received from the second application at a time corresponding to low glucose values. However, when the display uses a line with a different color or otherwise marks the line to indicate that the data was backfilled, the user can confirm that the second application did not have glucose values when the alarm should have occurred.

While the embodiments in FIGS. 8, 9A, and 9B have been described as backfilling a second application, it will be appreciated that the continuous glucose sensor unit 100 can also provide the first application, second application, or dedicated display 104 backfilled data directly. For example, dedicated display 104 or display 106 may be out of wireless range from the continuous glucose sensor unit 100. In another example, the user may turn off the dedicated application 108. In either situation, the dedicated display 104 or dedicated application 108 may not have current glucose values. The continuous glucose sensor unit 100 may detect that the glucose values are out of date and provide backfilled data over a defined time period in the same manner as described in FIG. 8. That is, the continuous glucose sensor unit 100 may transmit data beginning from the last time it received a confirmation that dedicated display 104 or display 106 received the glucose data. Alternatively or additionally, the dedicated display 104 or display 108 may detect that it only stores old data and request a backfill of glucose values over a given time period.

Figure 10:
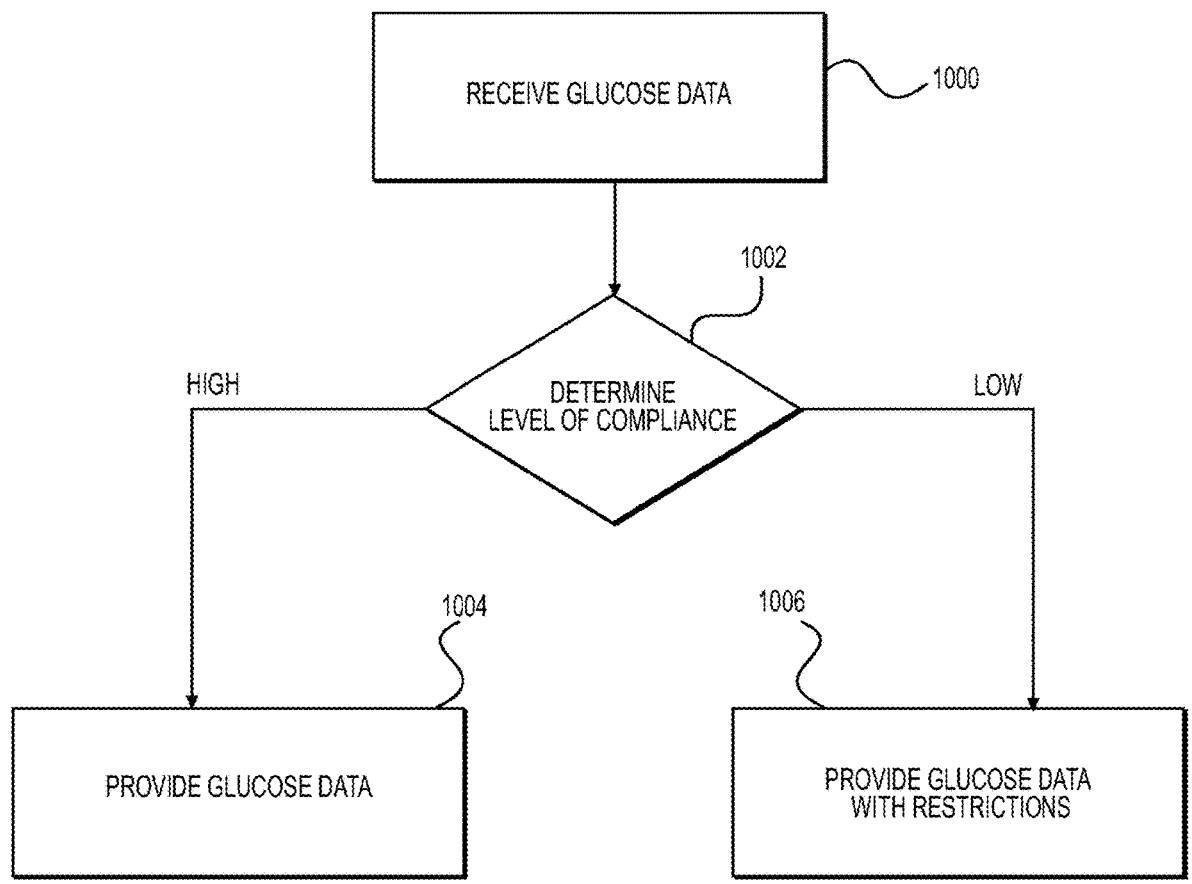
FIG. 10 illustrates an exemplary method for determining a level of compliance for a medical device and providing data relating to glucose levels to the medical device based on the level of compliance.

FIG. 10 illustrates an exemplary method for determining a level of compliance for a medical device and providing data relating to glucose levels to the medical device based on the level of compliance. The example of FIG. 10 illustrates a way to control the type of data that is provided to other applications based on the level of compliance of other applications. This ensures that the dedicated application 108 provides data only to trusted applications, or provides a reduced set of data to certain application compared to others.

At process 1000, the display 106 receives glucose data from continuous glucose sensor unit 100 as previously described. At process 1002, the dedicated application 108 determines a level of compliance of another application or a third-party requesting access to the data relating to glucose levels. The dedicated application 108 can determine the level of compliance in a variety of manners. For example, dedicated application 108 accesses a listing of applications stored in memory or online that indicates whether an application has been approved as a medical device by the Food and Drug Administration and, if so, a corresponding classification for the medical device. In another embodiment, the application may provide an indication of its classification and security level to the dedicated application 108.

If the level of compliance for an application is high, such as a class III medical device, the dedicated application 108 provides the glucose data to the application at process 1004. For example, the dedicated application 108 can provide the application with data relating to glucose levels in real-time. If, however, the level of compliance is lower, such as when the application is not a medical device, the dedicated application 108 provides data relating to glucose levels with restrictions at process 1006. For example, the restrictions may include encrypting data, providing a reduced set of data, delaying data, or any combination of the embodiments previously described with reference to FIGS. 1-10. In both situations of providing data without restrictions at process 1004 or providing data with restrictions at process 1006 (e.g., as described with reference to FIGS. 2, 5, and/or 7), a user may control preferences that determine which application should receive data and what set of data should be provided.

Figure 11:
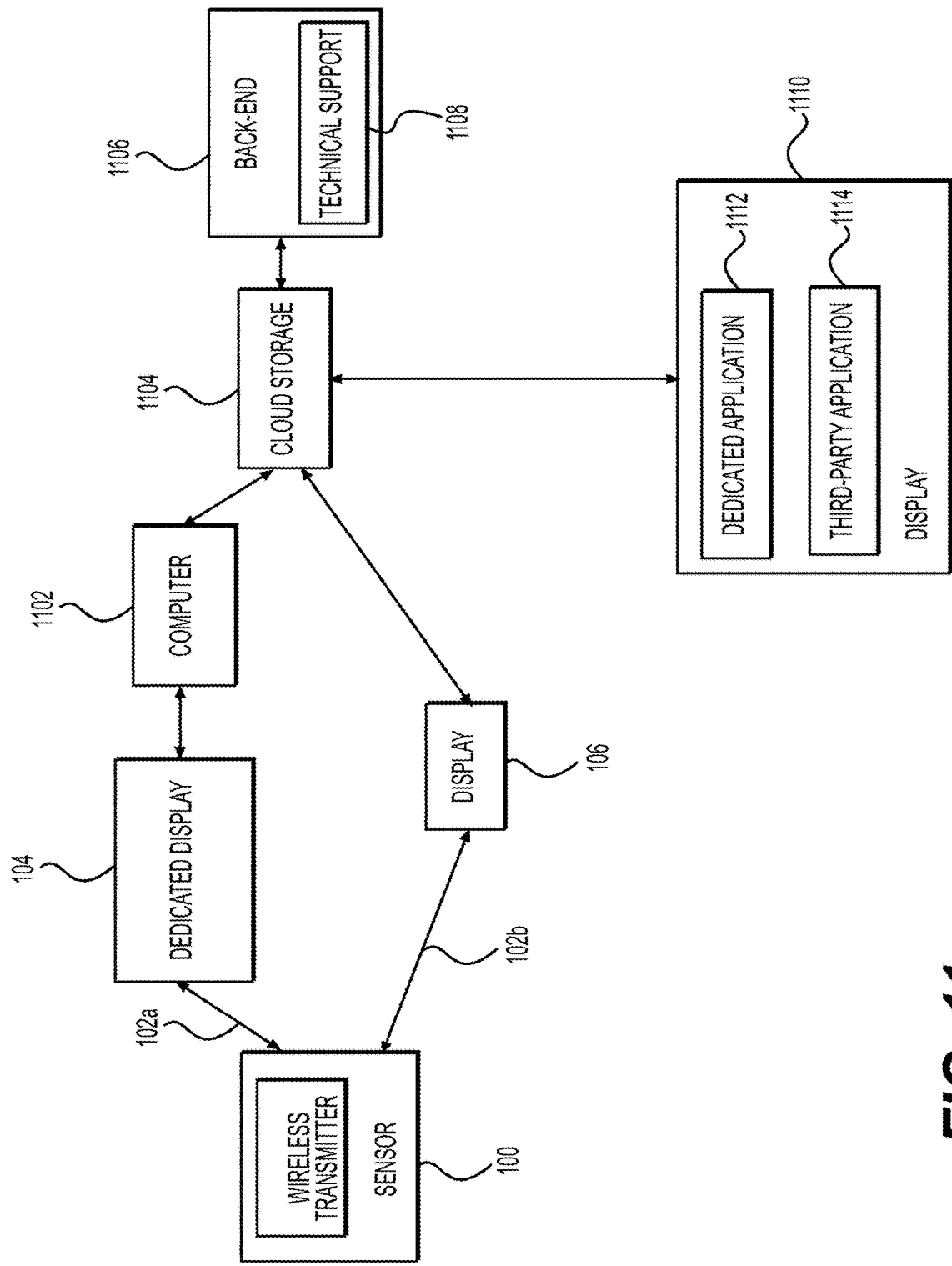
FIG. 11 illustrates an exemplary system for monitoring glucose levels.

FIG. 11 illustrates an exemplary system for monitoring glucose levels. The system of FIG. 11 may be used in conjunction with the system of FIG. 1 and the previously described embodiments. In particular, any of the disclosed methods can be used with any of the disclosed systems. However, it will be appreciated that the disclosed methods can be used with other system structures, and the disclosed systems implement other methods.

As in the embodiment of FIG. 1, the system shown in FIG. 11 includes a continuous glucose sensor unit 100, wireless connections 102a-b, a dedicated display 104, and one or more displays 106 executing applications. The dedicated display 104 may be connected using either a wired or wireless connection to computer 1102. Computer 1102 may be, for example, a personal computer, tablet, laptop, smart phone, or server. In addition, dedicated display 104 may connect to display 106, and display 106 may connect to computer 1102.

Computer 1102 and display 106 may connect to cloud storage 1104, which may provide long-term storage of data relating to glucose values, health information, system calibrations, and other information relating to continuous glucose monitoring. Cloud storage 1104 includes a plurality of storage devices, computers, and network connections. Communications between dedicated display 104, computer 1102, display 106, and cloud storage 1104 may use encryption to prevent unauthorized access to medical data.

Cloud storage 1102 connects to a back-end system 1106. The back-end system 1106 provides technical support 1108 for a user in configuring and using the continuous glucose monitor. The back-end system 1106 also monitors system information, such as versions of software executing on continuous glucose monitor 100, dedicated display 104, display 106, and computer 1102. The back-end system 1106 provides updates on demand or pushes updates to the dedicated display 104, display 106, continuous glucose sensor unit 100, and other system components using network connections in a secure fashion.

Another display 1110 may also connect to cloud storage 1102. The display 1110 may include a dedicated application 1112 and one or more third-party applications 1114, similar to those previously described. A user of continuous glucose sensor unit 100 may allow additional people to monitor their glucose levels and other health information. For example, a child may wear the continuous glucose monitor and have an associated dedicated display 104 and display 106. The child may designate one or both of their parents as additional users who can access the child's glucose levels and other health information using display 1110. The display 1110 may be, for example, the parent's smart phone.

The dedicated display 104 or display 106 provides continuous glucose data to cloud storage 1104. Cloud storage 1104, back-end system 1106, and/or display 1102 can monitor the continuous glucose data. The display 1102 receives and displays continuous glucose values as described previously, either without restriction as with dedicated application 108 or subject to restrictions as with third-party applications. The restrictions may be set by dedicated display 104 or display 106 in some embodiments. In other embodiments, display 1110 sets restrictions for data it receives through an authenticated process between the user of continuous glucose monitor 100, the user of display 1100, and back-end system 1106. For example, a user may contact the back-end system (e.g., by computer or telephonic communication) to establish authentication, such as call a representative of technical support 1108 and answer security questions before establishing the appropriate operation of the system, or conduct the process online. Once complete, the user of continuous glucose sensor unit 100 or the user of display 1110 may be restricted in the data their device receives or their ability to change system operation. This can prevent dedicated display 104 or display 106 from restricting monitoring by display 1110. For example, some situations can occur when the user of the sensor unit 100 and/or display 104 or 106 may wish to restrict the monitor using display 1110 who must maintain responsible monitoring continuously, such as when a child may eat a lot of sweet food at a birthday party that can cause a spike in glucose levels. The disclosed processes and controls of user authentication and data access accounts for a variety of use cases, such as the previous example.

Figure 12:
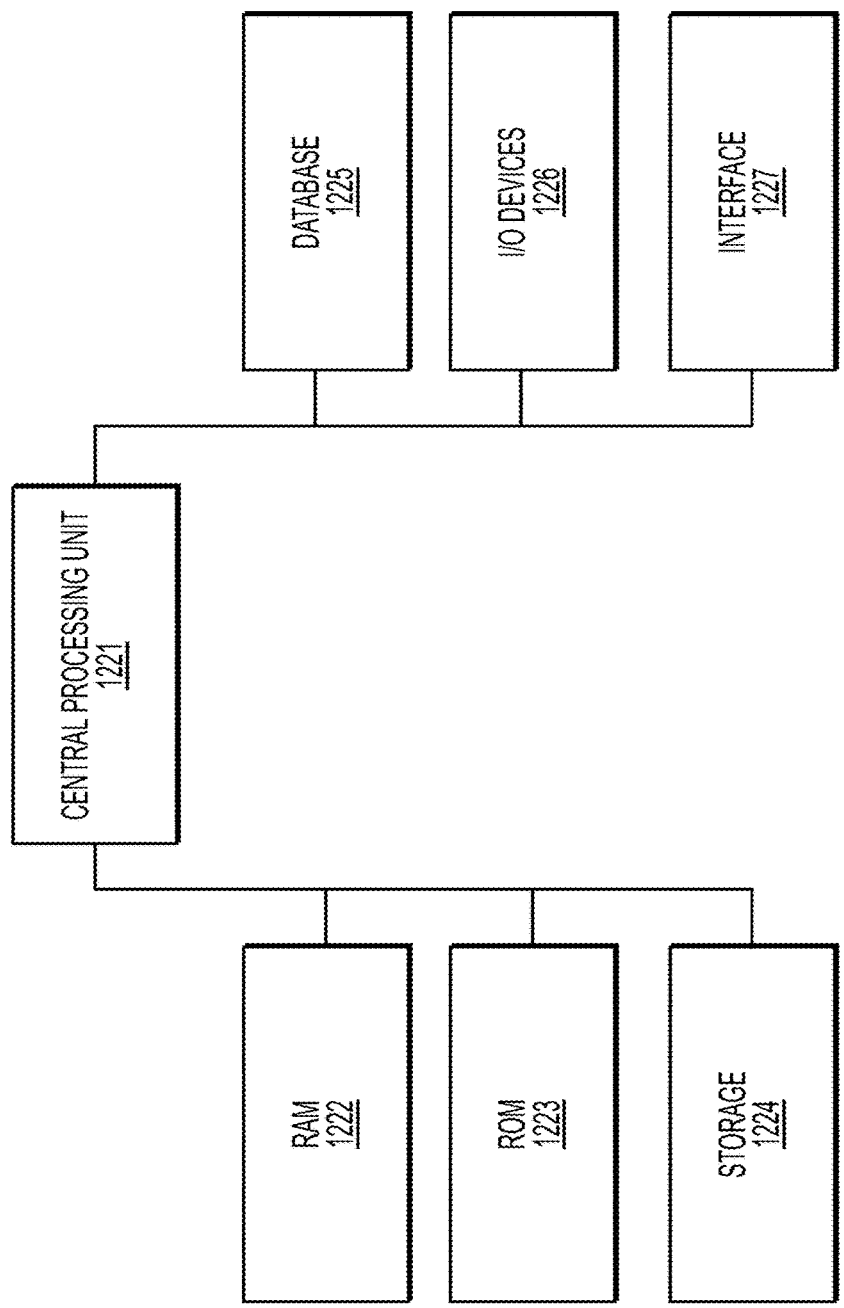
FIG. 12 illustrates an exemplary computer for monitoring glucose levels.

FIG. 12 illustrates an exemplary computer for monitoring glucose levels. Continuous glucose sensor unit 100, dedicated display 104, display 106, computer 1102, cloud storage 1104, back-end system 1106, and display 1110 may all include the components shown in FIG. 12.

The computers may include one or more hardware components such as, for example, a central processing unit (CPU) 1221, a random access memory (RAM) module 1222, a read-only memory (ROM) module 1223, a storage 1224, a database 1225, one or more input/output (I/O) devices 1226, and an interface 1227. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 1224 may include a software partition associated with one or more other hardware components. It is understood that the components listed above are exemplary only and not intended to be limiting.

CPU 1221 may include one or more processors, each configured to execute instructions and process data to perform one or more functions associated with a computer for monitoring glucose levels. CPU 1221 may be communicatively coupled to RAM 1222, ROM 1223, storage 1224, database 1225, I/O devices 1226, and interface 1227. CPU 1221 may be configured to execute sequences of computer program instructions to perform various processes. The computer program instructions may be loaded into RAM 1222 for execution by CPU 1221.

RAM 1222 and ROM 1223 may each include one or more devices for storing information associated with operation of CPU 1221. For example, ROM 1223 may include a memory device configured to access and store information associated with controller 1220, including information for identifying, initializing, and monitoring the operation of one or more components and subsystems. RAM 1222 may include a memory device for storing data associated with one or more operations of CPU 1221. For example, ROM 1223 may load instructions into RAM 1222 for execution by CPU 1221.

Storage 1224 may include any type of mass storage device configured to store information that CPU 1221 may need to perform processes consistent with the disclosed embodiments. For example, storage 1224 may include one or more magnetic and/or optical disk devices, such as hard drives, CD-ROMs, DVD-ROMs, or any other type of mass media device.

Database 1225 may include one or more software and/or hardware components that cooperate to store, organize, sort, filter, and/or arrange data used by CPU 1221. For example, database 1225 may data relating to monitoring glucose levels, associated metadata, and health information. It is contemplated that database 1225 may store additional and/or different information than that listed above.

I/O devices 1226 may include one or more components configured to communicate information with a user associated with controller 1220. For example, I/O devices may include a console with an integrated keyboard and mouse to allow a user to maintain a database of images, update associations, and access digital content. I/O devices 1226 may also include a display including a graphical user interface (GUI) for outputting information on a monitor. I/O devices 1226 may also include peripheral devices such as, for example, a printer for printing information associated with controller 1220, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 1227 may include one or more components configured to transmit and receive data via a communication network, such as the Internet, a local area network, a workstation peer-to-peer network, a direct link network, a wireless network, or any other suitable communication platform. For example, interface 1227 may include one or more modulators, demodulators, multiplexers, demultiplexers, network communication devices, wireless devices, antennas, modems, and any other type of device configured to enable data communication via a communication network.

Any combination of one or more computer readable medium(s) may be utilized. The computer readable medium may be a computer readable signal medium or a computer readable storage medium. A computer readable storage medium may be, for example, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Program code embodied on a computer readable medium may be transmitted using any appropriate medium, including but not limited to wireless, wireline, optical fiber cable, RF, etc., or any suitable combination of the foregoing.

Computer program code for may be written in any combination of one or more programming languages, including an object oriented programming language such as Java, Smalltalk, C++, or the like, and conventional procedural programming languages, such as the "C" programming language or similar programming languages. The program code may execute entirely on the computing unit.

Figure 13:
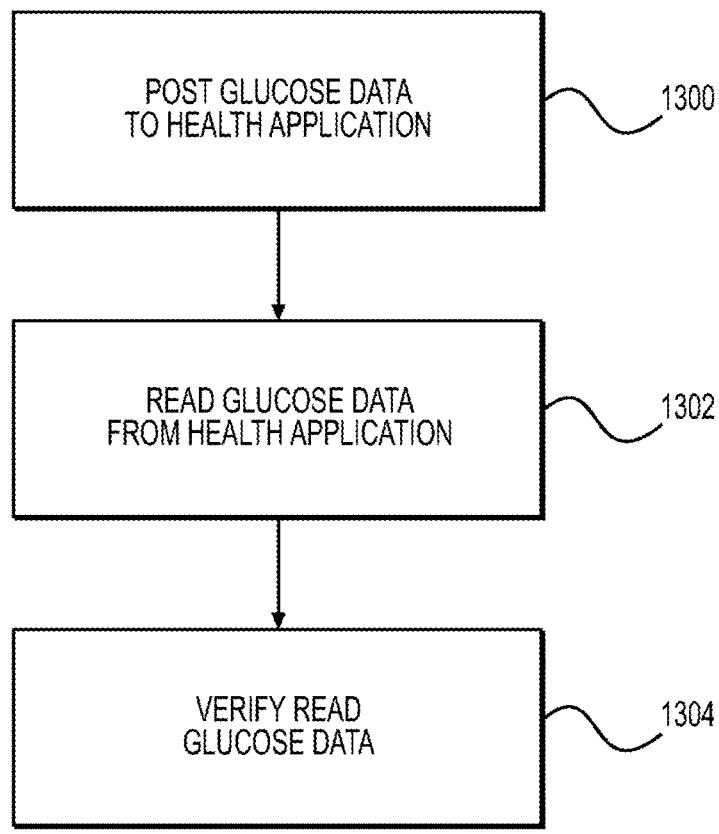
FIG. 13 illustrates an exemplary method for verifying the accuracy of information stored by a third-party application.

FIG. 13 illustrates an exemplary method for verifying the accuracy of information stored by a third-party application. When distributing sensitive medical data, a problem arises that the receiving party may not accurately store the data or may not even be storing the data at all due to a system error. This can lead to problems including false recommendations for glucose levels and confusion by a user when the receiving party displays different data from the providing party. In one example, the dedicated application 108 transmits data to a health application and needs to verify that the health application accurately received and stored the data.

At process 1300, the dedicated application 108 posts glucose data to a health application. The health application can be any type of application that receives glucose data from the dedicated application 108. The dedicated application 108 can post actual measured values or test data to the health application.

At process 1302, the dedicated application 108 reads back the glucose data from the health application. Application program interfaces can be used to request read data back from the health application. By reading back the posted values, the dedicated application 108 can verify that the data relating to glucose values was properly received, handled, and stored by the third-party health application at process 1304. If the read data does not match the posted data, the dedicated application 108 issues a notification to the user or determines that the health application should no longer receive data relating to glucose values. In one embodiment, the dedicated application 108 posts a predetermined test glucose value and time to the health application. The dedicated application 108 then reads back the glucose value associated with the predetermined time, and determines if the two match.

Figure 14:
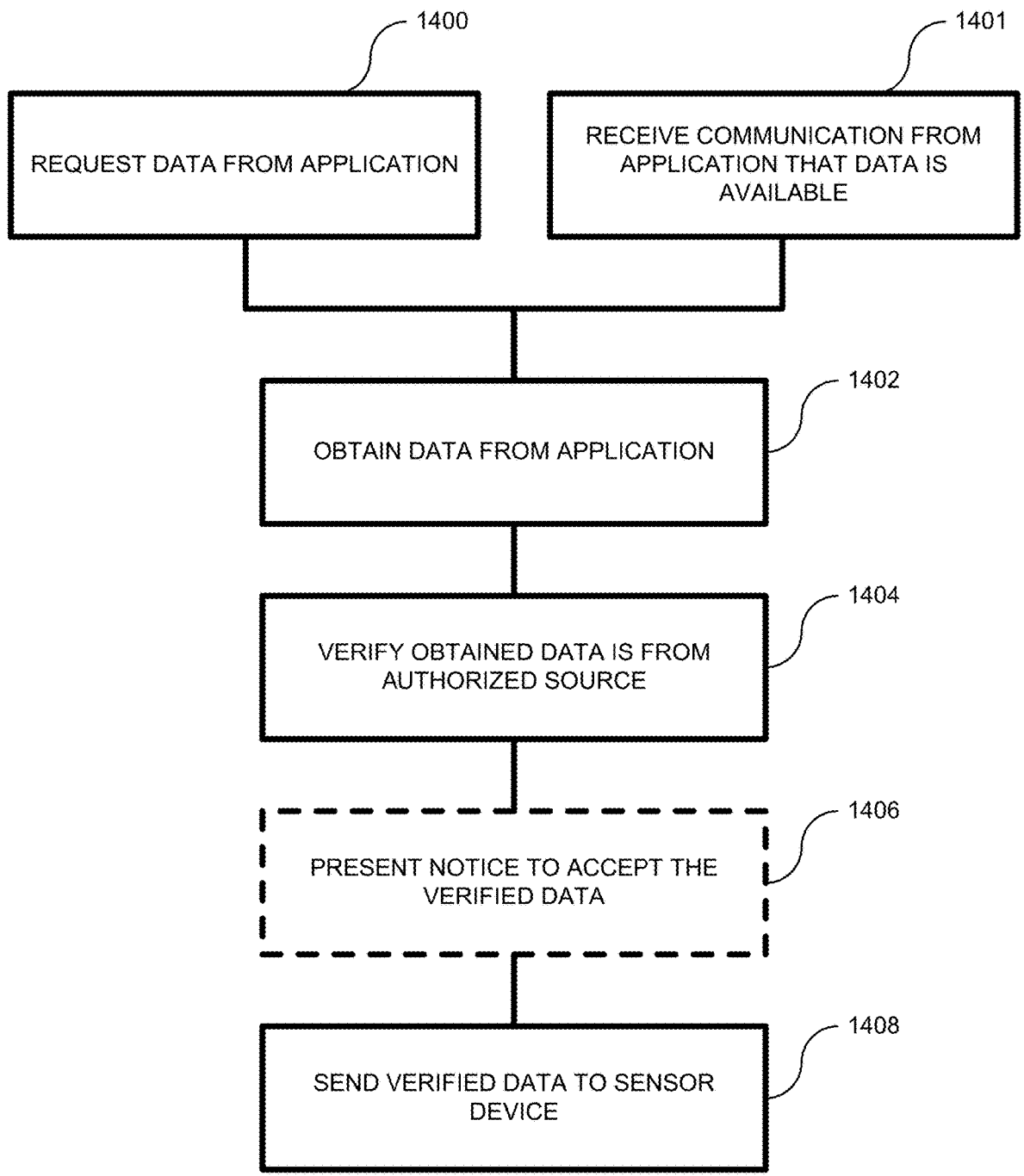
FIG. 14 illustrates an exemplary method for providing data to a dedicated application from a third-party application.

FIG. 14 illustrates an exemplary method for providing data to a dedicated application from a third-party application. The method can be used to verify whether the data and/or source of the data is authentic and trustworthy. Implementations of the method can allow the disclosed system to receive data from an external device or system in an automated manner with safeguards and which does not require manual input of data by the user. For example, the continuous glucose sensor unit 100 may require or benefit from inputting glucose values from an external glucose meter device, such as a single point blood glucose (BG) meter, for calibration on initial startup and/or a periodic calibration update or verification of the continuous glucose sensor unit 100 to maintain accuracy of the glucose measurements. In such cases, a user samples their glucose level using the blood glucose meter, which may send the user's test results to the user's mobile device (e.g., display 106) and/or the cloud. The BG value determined by the external blood glucose meter device may be used for initial or periodic calibration purposes of the continuous glucose sensor unit 100. The user's mobile device (e.g., display 106) includes an application (e.g., third-party application 112 or 114) that collects and stores at least temporarily the BG values, which may also be provided to a health application on the user's device (e.g., third-party health application 110). As discussed above, accurate glucose values for calibration of the continuous glucose sensor unit 100 is critically important, since inaccurate measurements could lead to a variety of potentially dangerous situations where a user takes action based on incorrect glucose readings and/or does not receive notifications or receives false-positive notifications about their physiological condition to take an appropriate action. Therefore, the method of FIG. 14 provides essential verification features in the transfer process of such data from a third-party application to the user's dedicated application associated with the continuous glucose sensor unit 100, while also creating convenience and safety to the user by automating the data transfer and minimizing risk of inaccurate data from user data entry error. For example, the method could reduce potential errors like the user reading a BG value of "68" (mg/dL) from the single point blood glucose meter and typing "98" (mg/dL) into the user interface of the mobile device (e.g., display 106) for calibration of the continuous glucose sensor unit 100.

At process 1400, dedicated application 108 requests data (e.g., blood glucose data) from a health application, also referred to as third-party health application 110 shown in FIG. 1 for this example. The health application 110 can be any type of application that receives the blood glucose data from a single point blood glucose meter, a data storage on a device or in the cloud, or via another application, also referred to as third-party applications 112, 114, or 116 shown in FIG. 1 for this example. In some implementations of the process 1400, the dedicated application 108 requests the data from the other third-party application 112, 114, or 116. The dedicated application 108 can request the data by accessing the health application 110 (or other third-party application in some implementations) through standardized application program interfaces. The dedicated application 108 can request the data from the health application 110 based on an occurrence of an event. The event can be, for example, a particular time or an amount of time since a previous data-request or event, the launching or opening of the dedicated application 108 or the health application 110, or other events. In a specific example, the dedicated application 108 accesses the health application 110 to request for the glucose data at a certain time in the morning and a certain time in the evening on a daily basis.

Additionally or alternatively, at process 1401, dedicated application 108 receives a communication from the health application 110 that data is available (e.g., blood glucose data) for retrieval. In some implementations of the process 1401, the dedicated application 108 receives the communication that the data is available from the other third-party application 112, 114, or 116.

At process 1402, dedicated application 108 obtains the blood glucose data from the health application 110 or other third-party application. In some implementations, the dedicated application 108 can obtain the data through standardized application program interfaces that provide a list of acceptable commands and the format for any responses with respect to the applications in communication with the dedicated application. For example, the dedicated application 108 can send a command such as: retrieve blood glucose value, and receive a response with two or more variables—one indicating the numeric value and associated unit of the blood glucose measurement and a timestamp when the measurement was acquired. While an example has been provided, it will be appreciated that other application program interfaces can be used to exchange information between the dedicated application 108 and third-party application. In some implementations, the health application 110 or operating system executing on the user's display 106 can push the blood glucose data to the dedicated application 108 after the process 1400 or 1401 or in response to the occurrence of any of the previously described events.

The obtained blood glucose data includes metadata associated with each blood glucose measurement, such as a unit of the measurement (e.g., concentration unit, such as mg/dL) a timestamp of when the measurement was acquired, a parameter associated with the measurement (e.g., such as information associated with the chemical analysis), a code associated with the external blood glucose meter device or test strips used by the meter, or the like.

At process 1404, dedicated application 108 verifies the blood glucose data obtained from the health application 110 or other third-party application to detect if it was derived from an authorized source. In some implementations, the dedicated application 108 analyzes the metadata to verify the source of the blood glucose measurement data. For example, the dedicated application 108 can process the metadata to identify one or more codes associated with the external blood glucose meter device or test strips used by the meter to check against a list of authorized devices and/or test strips to validate the authenticity of the blood glucose measurement data. If the identified code is a match to an authorized device or related component, then the dedicated application 108 approves the blood glucose data.

At optional process 1406, dedicated application 108 presents a notice to the user to accept the verified blood glucose data for calibration of the continuous glucose sensor unit 100. In some implementations, the notice is presented on the display screen of the user's device (e.g., display 106) executing the dedicated application 108 as a pop-up window of the dedicated application 108. In some implementations, the notice is presented on the user's device (e.g., display 106) as notification in the form of a banner, badge, sound, and/or alert via the operating system operating on the user device. In some implementations, the notice to the user via a text message, email, IM, automated phone call or other communication. In some embodiments, the notice includes an option for the user to respond affirmatively or negatively for acceptance of the verified blood glucose data and/or an option for the user to manually enter the blood glucose data. If the user responds negatively or chooses to enter blood glucose data manually, the dedicated application 108 can provide an interface to receive the user's data entry of the blood glucose data.

Figure 15:
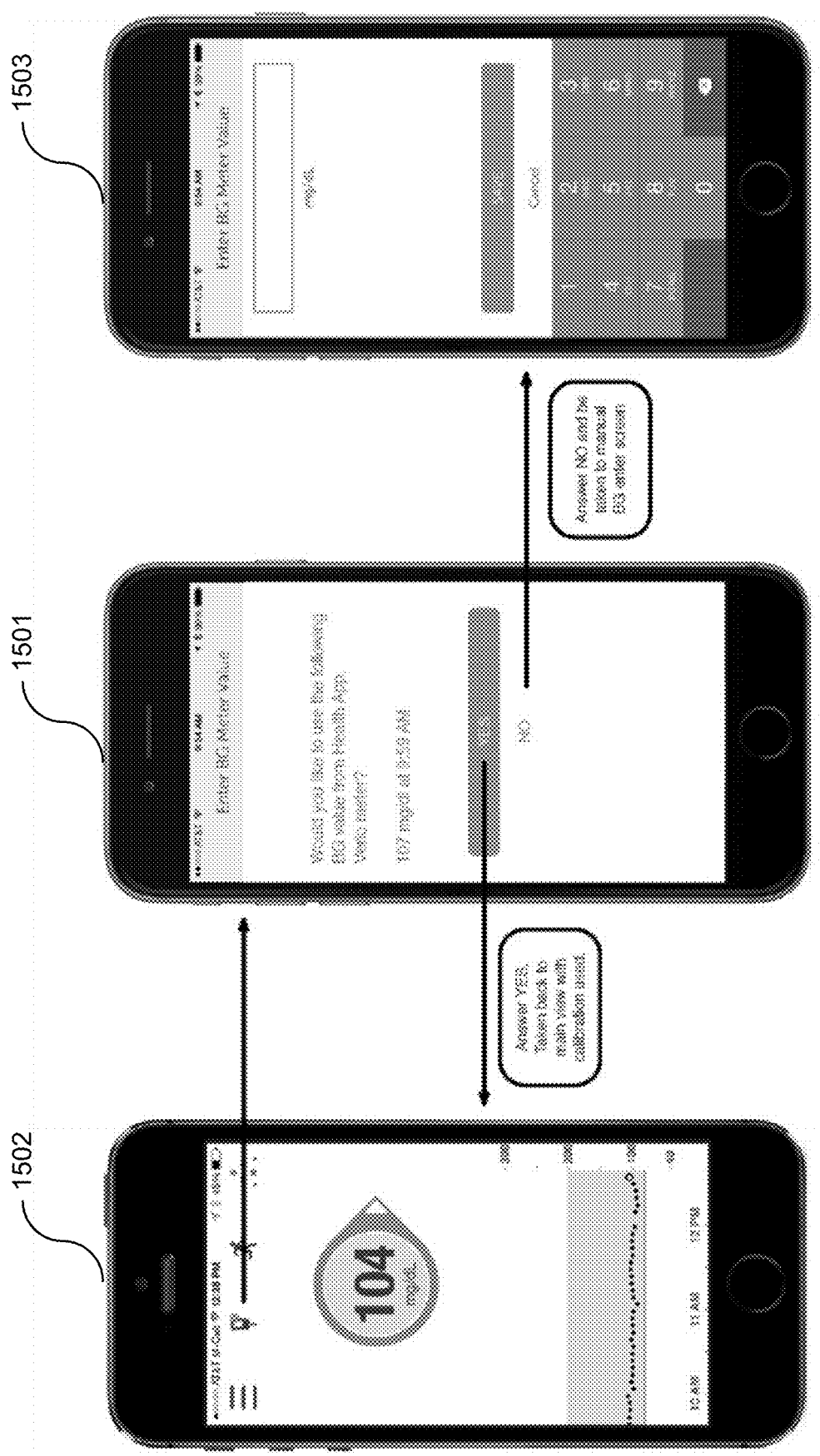
FIG. 15 shows a diagram depicting an example user interface presenting a notice for a user to accept the verified data for calibration of a sensor device.

FIG. 15 shows a diagram depicting an example user interface of the dedicated application 108 presenting a notice to accept the verified blood glucose data for calibration of the user's continuous glucose sensor unit. In display screen 1501, the user interface presents the option for the user to respond affirmatively ("Yes") or negatively ("No") for the dedicated application 108 to use the verified blood glucose data, shown in this example to have been obtained a BG value of "107 mg/dl at 9:59 AM" from "Health App" derived from the "Verio meter." If the user selects "Yes", then the user interface displays display screen 1502 that depicts a return to the main view of the dedicated application 108, shown in this example to display the current glucose value and trend from the continuous glucose sensor unit 100. If the user selects "No", then the user interface displays display screen 1503 that depicts a prompt to enter the BG meter value to be used for calibration.

Figure 16:
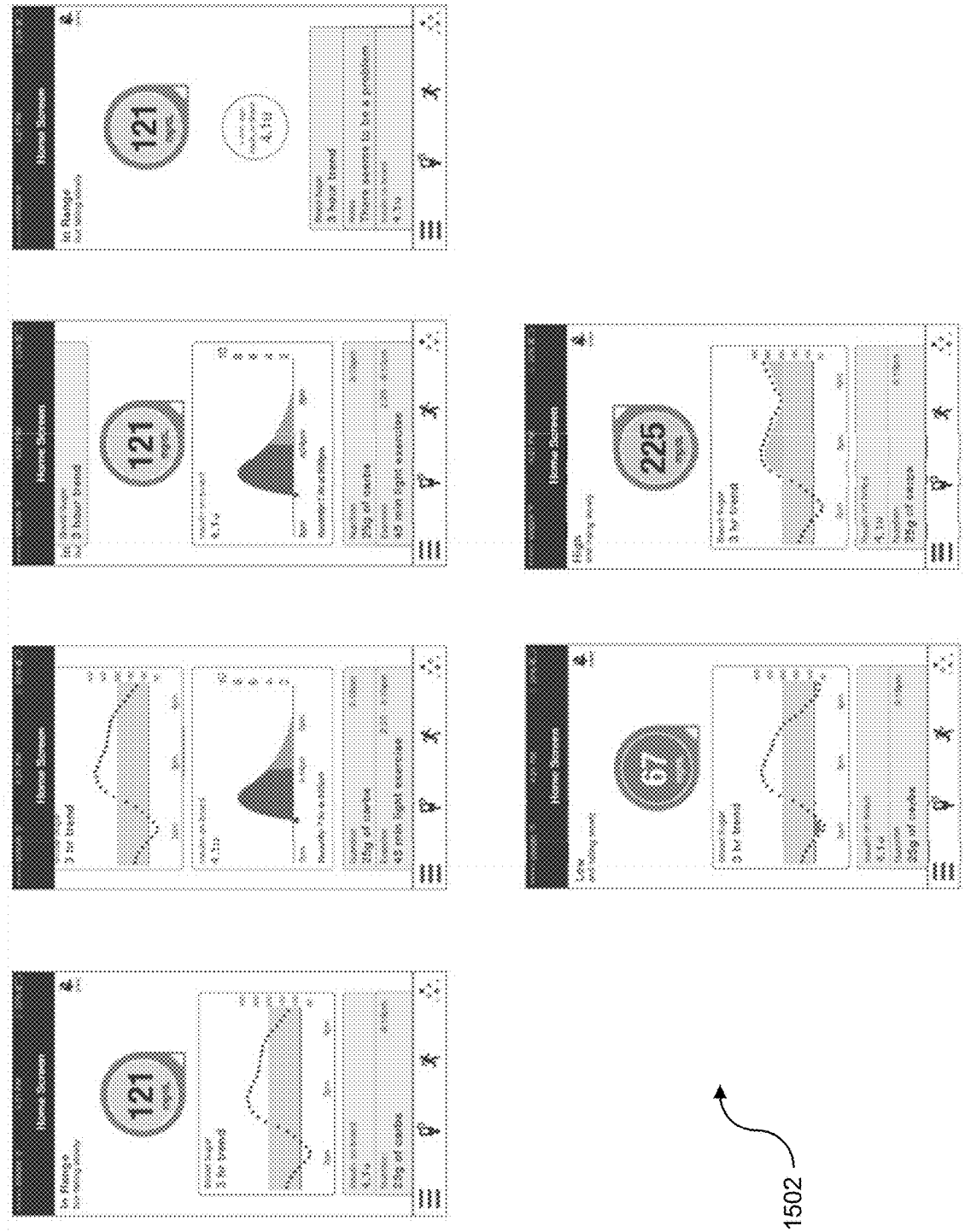
FIG. 16 shows illustrations of example display screens of a home screen for a dedication application associated with a continuous analyte sensor device.

FIG. 16 shows illustrations of other example display screens of a home screen or main view 1502 of the dedicated application 108. In the examples shown in FIG. 16, the home screen may present health information such as insulin on board, exercise, and nutrition information in various formats including text and/or graphical interfaces. Such health information can be presented proximate to the glucose data provided by the continuous glucose sensor unit 100, which can be presented as previously described with respect to FIGS. 4, 6A, 9A and 9B.

Referring back to FIG. 14, at process 1408, dedicated application 108 sends the verified data to the continuous glucose sensor unit 100.

Figure 17:
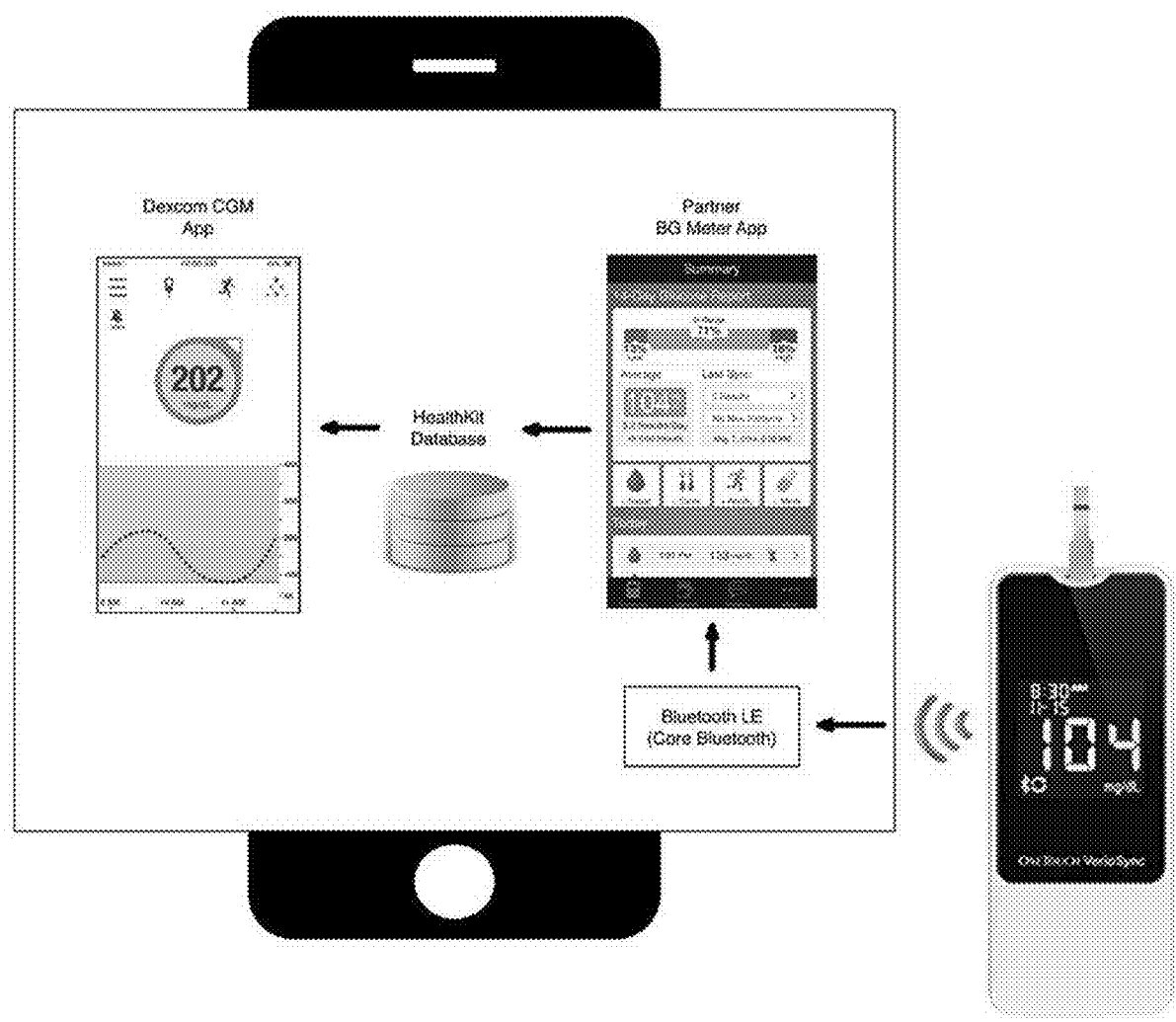
FIG. 17 shows an illustrative diagram of the data flow between an external sensor device and a dedicated application on a user's mobile device.

FIG. 17 shows an illustrative diagram of the data flow between an external sensor device (e.g., single point blood glucose meter) and the dedicated application 108 on the user's device (e.g., in this smart phone in this example). As shown in the diagram, the single point blood glucose meter wirelessly transfers blood glucose data to a third-party application (e.g., such as approved third-party application 116 shown in FIG. 1), e.g., for processing, storage, display and/or other purposes. The third-party application then provides the blood glucose data to the dedicated application 108 via a health application operating on the user's device. For example, upon receiving the blood glucose data from the third-party application, the health application can store the blood glucose data in a storage in the cloud and manage the storage and accessibility using a database of the health application. The health application can provide the blood glucose data to the dedicated application in accordance with the method of FIG. 14.

Figure 18:
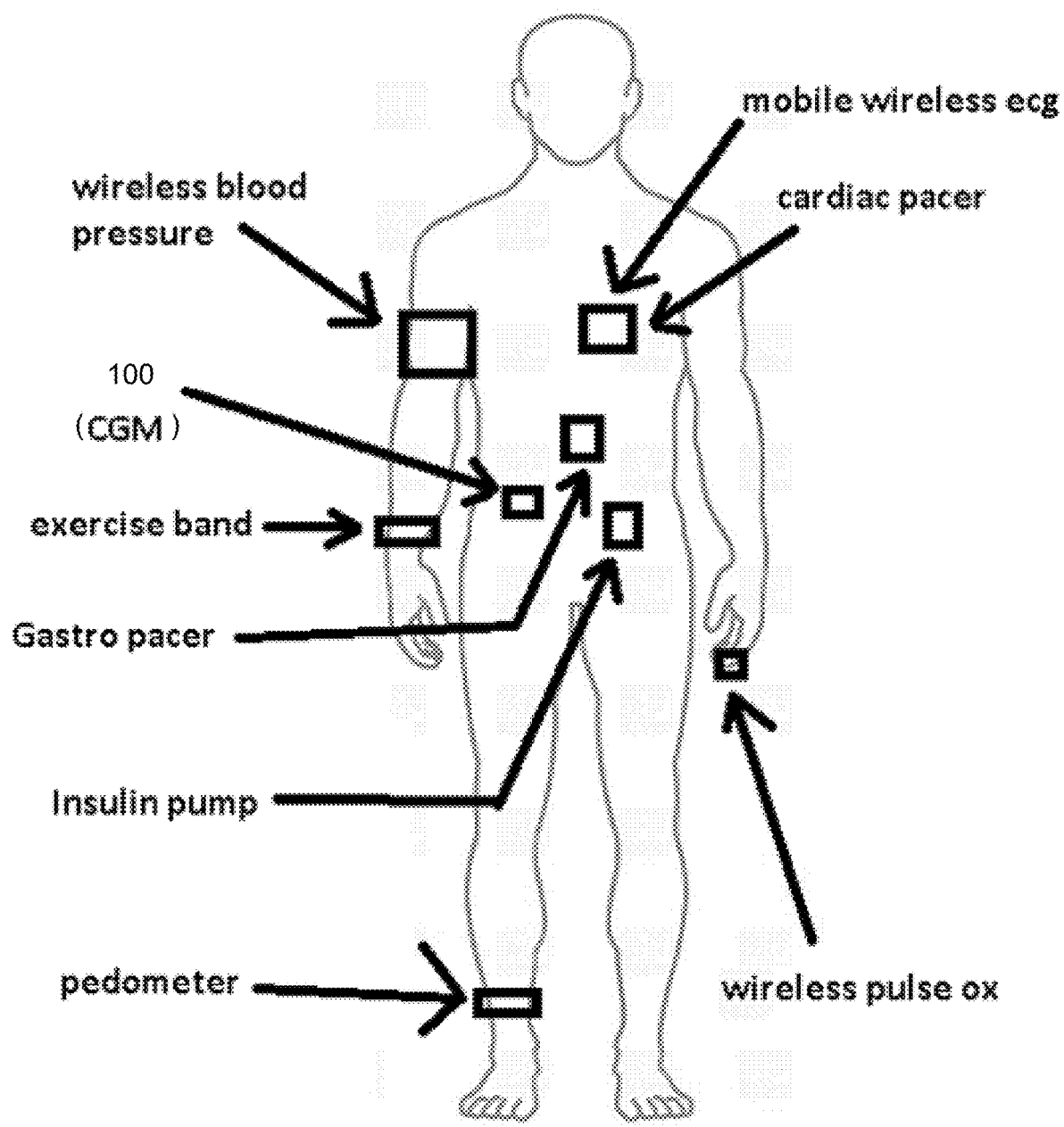
FIG. 18 shows a diagram of a user employing multiple body-worn sensor and/or actuator devices that provide health information relevant to glucose data monitored by a continuous glucose sensor unit.

FIG. 18 shows a diagram of a user employing multiple body-worn sensor and/or actuator devices that can provide health information relevant to glucose data monitored by the continuous glucose sensor unit 100. Examples of the body-worn sensor devices include medical devices such as a pedometer, a pulse oximeter, an insulin pump, a gastro pacer, a blood pressure monitor, an ECG monitor, and a cardiac pacemaker, and the like. In the example of FIG. 18, the user is wearing the continuous glucose sensor unit 100, which communicates via BLE to the user's mobile device (e.g., display 106, such as a smart phone) in which the data received from the sensor unit 100 is managed by the dedicated application 108. The user is also employing an insulin pump that communicates with the user's smart phone using a third-party application, e.g., such as third-party applications 110~116. In a closed loop environment, tertiary sensors and devices are not taken into account. However, if third-party applications directly or indirectly associated with these tertiary sensors and devices residing on the smart phone is able to connect and interact with the dedicated application, then information collected and/or processed by the third-party applications can be included and utilized by the dedicated application for the user's health management. For example, the associated third-party application with a heart rate monitor (HRM) may aggregate information from the HRM and provide that information to a health application or the dedicated application of the sensor unit 100. Using techniques described above, the heart rate data may be stored and displayed in concurrence with the sensed glucose information from the continuous glucose sensor unit 100. In this manner, for example, the patient user may view and infer knowledge from this information. Also, for example, secondary viewers may be provided access to the information, such as health care providers, who may utilize said information as determined by the provider for various purposes ranging from informational to analysis of the data.

Furthermore, for example, if the patient user utilizes an exercise monitor such as a BLE pedometer or other exercise related device, the dedicated application 108 and/or health application 110 can aggregate the pedometer data into a comprehensive data set including the glucose data, HRM data, and other sensor or actuator data. Illustratively, in such events, when exercise does occur and the exercise sensor provides the information to the user's mobile device, the information acquired from the exercise device is aggregated within the data set and analyzed to align or associate information from the exercise data with such things as sensed glucose level. Therefore, the patient user would not be required to enter notations or event markers within their glucose monitoring application, as this occurs automatically by the disclosed system environment.

The disclosed system environment can provide automated data entry of events and activities in significant detail and granularity that may be inconvenient or impossible for the patient user to do on their own and as it occurs at its determined interval. For example, the determined interval may be such as a predetermined interval or timed event such as beats per minutes at a granularity of 15 second intervals or calories burned per 30 seconds, in which a threshold value over that interval may trigger the automated data entry of the event with the glucose data in accordance with the techniques described in this patent document.

Also, such aggregated information from the tertiary sensor and/or actuator devices may provide information regarding potential motion artifacting of gathered data from other sensing devices including the continuous glucose sensor unit 100. This motion artifacting may be in the form of true/false presence and/or a data confidence level and/or a value in a scale. This information may be sent or provided to the continuous glucose sensor unit 100 or a technical support service for the sensor unit 100, e.g., via the dedicated application 108 or health application 110, for further processing and decision making and/or as input into data processing algorithms.

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Although the term first application has been referred to as dedicated application 108, it will be appreciated that a first application may be any of third-party application 110~116 or another application. Similarly, while the second application has been referred to as approved third-party application 110 and a health application, the second application may also be dedicated application 108, any of third-party applications 112~116, or another application. Moreover, while certain applications 110~116 have been described as third-party applications, it will be appreciated that applications 110~116 need not be provided by third-parties.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

The following examples are illustrative of several embodiments of the present technology. Other exemplary embodiments of the present technology may be presented prior to the following fisted examples, or after the following listed examples In some embodiments of the present technology (example 1), a method for monitoring glucose values includes receiving, at a first application operable on a mobile computing device, health data including a glucose measurement and associated timestamp transmitted over a wireless connection; determining, by the first application, that a time duration between a current time and the timestamp meets a predetermined amount of delay; and providing, by the first application, the glucose measurement to a second application operable on the mobile computing device only after the predetermined amount of delay.

Example 2 includes the method of example 1, wherein the first application includes a medical device software application that configures the mobile computing device to receive and process glucose data including the glucose measurement provided by a continuous glucose monitoring sensor device, and wherein the second application includes a third-party software application.

Example 3 includes the method of example 2, wherein the third-party software application is configured to provide at least some capabilities different than that of the first application including processing ancillary data and integrating the ancillary data with the glucose data, wherein the ancillary data includes one or more of insulin data, meal data, or exercise data.

Example 4 includes the method of example 2, wherein the third-party software application is not an approved medical device software application approved by a governmental regulatory institution authorized to regulate medical device technologies.

Example 5 includes the method of example 1, wherein the received health data includes a plurality of continuously generated glucose measurements and associated timestamps for each glucose measurement; and the method includes delaying each of the plurality of continuously generated glucose measurements for the predetermined amount of time; and providing each of the plurality of continuously generated glucose measurements to the second application after the delaying.

Example 6 includes the method of example 1, wherein the glucose measurement is provided to the second application, after the predetermined amount of time, in response to the second application being executed by the mobile computing device.

Example 7 includes the method of example 1, wherein the delay is between five minutes and three hours.

Example 8 includes the method of example 1, further including obtaining metabolic health information affecting glucose levels; and displaying, using the first application, the glucose measurement concurrently with the metabolic health information, wherein the metabolic health information is obtained by the first application from the second application.

Example 9 includes the method of example 8, wherein the metabolic health information indicates an amount of activity determined using motion data produced by an accelerometer of the mobile computing device; or the metabolic health information comprises at least one of meal intake, exercise, or insulin injection.

Example 10 includes the method of example 5, further including creating from the received health data, by the first application, a set of data relating to the continuously generated glucose measurements; dividing, by the first application, the set of data by generating a first set of data and a second set of data according to a predetermined criteria; restricting access to the second set of data to the second application; and providing the first set of data to the second application.

Example 11 includes the method of example 10, wherein the dividing the set of data into the first set of data includes averaging the continuously generated glucose measurements over a predetermined interval to produce glucose average values to be in the first set of data.

Example 12 includes the method of example 10, wherein the dividing the set of data into the first set of data includes generating generalized indications of the continuously generated glucose measurements over a predetermined interval to be in the first set of data, wherein a generalized indication is representative of the continuously generated glucose measurements being in one of a predefined low range, a predefined normal range, and a predefined high range.

Example 13 includes the method of example 1, further including encrypting the glucose measurement prior to the providing the glucose measurement to the second application; transmitting an instruction for the second application to provide the encrypted measurement to a third application operable on the mobile computing device; and providing a key to decrypt the encrypted measurement to the third application.

Example 14 includes the method of example 13, wherein the providing includes providing the key to the second application with a communication for the second application to provide the key to the third application.

Example 15 includes the method of example 1, wherein the first application is configured to process glucose data associated with a continuous glucose sensor device; and the method further comprises receiving from a third-party application, at the first application, one or more single glucose measurements acquired from a single-measurement glucose sensor device; analyzing, by the first application, metadata corresponding to the one or more single glucose measurements; and authenticating, by the first application, the one or more single glucose measurements as calibration data for the continuous analyte sensor device.

In some embodiments of the present technology (example 16), a system for monitoring glucose values includes a sensor configured to obtain a glucose measurement of an amount of glucose; a wireless transmitter to transmit the glucose measurement and a timestamp associated with the glucose measurement; and a mobile computing device. The mobile computing device includes a wireless receiver configured to receive the glucose measurement, a memory to store data including the received glucose measurement, a processor to process the data, and a first software application including instructions stored in the memory which, when executed by the processor, determines when a time duration between a current time and the timestamp meets a predetermined amount of delay, and upon determination the time duration meets the predetermined amount of delay, provides the glucose measurement to a second software application on the mobile computing device, wherein the second software application is operable to receive the glucose measurement when provided by the first software application after the predetermined amount of delay.

Example 17 includes the system of example 16, wherein the first software application includes a medical device software application that configures the mobile computing device to receive and process the glucose measurement received from the sensor, and wherein the second software application includes a third-party software application.

Example 18 includes the system of example 17, wherein the third-party software application is configured to provide at least some capabilities different than that of the first software application including processing ancillary data and integrating the ancillary data with the glucose measurement, wherein the ancillary data includes one or more of insulin data, meal data, or exercise data.

Example 19 includes the system of example 17, wherein the third-party software application is not an approved medical device software application approved by a governmental regulatory institution authorized to regulate medical device technologies.

Example 20 includes the system of example 16, wherein the glucose measurement is provided to the second software application, after the delay, in response to the second software application being executed.

Example 21 includes the system of example 16, wherein the delay is between five minutes and three hours.

Example 22 includes the system of example 16, wherein the wireless receiver of the mobile computing device is configured to receive a plurality of continuously generated glucose measurements and a timestamp associated with each continuously generated glucose measurement; the memory of the mobile computing device is configured to store the plurality of continuously generated glucose measurements; and the first software application includes instructions, which when executed by the processor, causes the mobile computing device to delay each of the plurality of continuously generated glucose measurements for the predetermined amount of time, and provide each of the plurality of continuously generated glucose measurements to the second software application after the delay.

Example 23 includes the system of example 22, wherein the first software application includes instructions, which when executed by the processor causes the mobile computing device to create a set of data relating to the continuously generated glucose measurements; divide the set of data by generating a first set of data and a second set of data according to a predetermined criteria; restrict access to the second set of data to the second software application; and provide the first set of data to the second software application.

Example 24 includes the system of example 23, wherein the generating the first set of data includes averaging the continuously generated glucose measurements over a predetermined interval to produce glucose average values to be in the first set of data.

Example 25 includes the system of example 23, wherein the generating the first set of data includes generating generalized indications of the continuously generated glucose measurements over a predetermined interval to be in the first set of data, wherein a generalized indication is representative of the continuously generated glucose measurements being in one of a predefined low range, a predefined normal range, and a predefined high range Example 26 includes the system of example 16, wherein the first software application includes instructions, which when executed by the processor causes the mobile computing device to encrypt the glucose measurement prior to providing the glucose measurement to the second software application; transmit an instruction for the second software application to provide the encrypted measurement from the second software application to a third software application operable on the mobile computing device; and provide a key to the third software application to decrypt the encrypted measurement.

In some embodiments of the present technology (example 27), a medical device software application for managing glucose data received from a glucose sensor is disclosed. The medical device software application is on a computer-readable medium of a mobile computing device, and includes instructions which, when executed by a processor of the mobile computing device, causes the mobile computing device to receive one or more glucose measurements generated by the glucose sensor, wherein the one or more glucose measurements include an associated timestamp; assign the received one or more glucose measurements as retrospective glucose data or actionable glucose data based on a predetermined amount of time difference between the timestamp and a current time; and provide the retrospective glucose data to a third-party software application operable on the mobile computing device.

Example 28 includes the medical device software application of example 27, wherein the third-party software application is not an approved medical device software application approved by a governmental regulatory institution authorized to regulate medical device technologies.

Example 29 includes the medical device software application of example 27, wherein the third-party software application is configured to provide at least some capabilities different than that of the medical device software application including processing ancillary data and integrating the ancillary data with the retrospective glucose data, wherein the ancillary data includes one or more of insulin data, meal data, or exercise data.

Example 30 includes the medical device software application of example 27, wherein the medical device software application includes instructions, which when executed by the processor, causes the mobile computing device to create a set of data relating to the one or more glucose measurements; divide the set of data by generating a first set of data and a second set of data according to a predetermined criteria; restrict access to the first set of data to the third-party software application; and provide the second set of data to the third-party software application.

Example 31 includes the medical device software application of example 27, wherein the medical device software application includes instructions, which when executed by the processor, causes the mobile computing device to encrypt the received one or more glucose measurements or the assigned retrospective glucose data prior to providing the retrospective glucose data to the third-party software application; transmit an instruction for the third-party software application to provide the encrypted retrospective glucose data to a second third-party software application operable on the mobile computing device; and provide a key to the second third-party software application to decrypt the encrypted retrospective glucose data.

In some embodiments of the present technology (example 32), a method for controlling distribution of data relating to glucose levels between applications executing on a computing device includes receiving, at a mobile computing device, a plurality of data values relating to glucose level monitoring; separating, at a first application operable on the mobile computing device, the plurality of data values into a first set of data and a second set of data according to a predetermined criteria, the first set of data comprising data values restricted from the second set of data; and providing the second set of data to a second application operable on the mobile computing device.

Example 33 includes the method of example 32, wherein the first application includes a medical device software application that configures the mobile computing device to receive and process glucose data including the data values relating to the glucose level monitoring provided by a continuous glucose monitoring sensor device, and wherein the second application includes a third-party software application.

Example 34 includes the method of example 33, wherein the third-party software application is configured to provide at least some capabilities different than that of the first application including processing ancillary data and integrating the ancillary data with the glucose data, wherein the ancillary data includes one or more of insulin data, meal data, or exercise data.

Example 35 includes the method of example 33, wherein the third-party software application is not an approved medical device software application approved by a governmental regulatory institution authorized to regulate medical device technologies.

Example 36 includes the method of example 32, wherein the plurality of data values are separated into the first set of data and the second set of data based on predetermined data permissions associated with the second application.

Example 37 includes the method of example 32, wherein the received plurality of data values include continuously generated glucose measurements, and wherein the separating the plurality of data values further includes averaging the continuously generated glucose measurements over a predetermined interval to produce glucose average values to be in the second set of data.

Example 38 includes the method of example 32, wherein the received plurality of data values include continuously generated glucose measurements, and wherein the separating the plurality of data values further includes generating generalized indications of the continuously generated glucose measurements over a predetermined interval to be in the second set of data, wherein a generalized indication is representative of the continuously generated glucose measurements being in one of a predefined low range, a predefined normal range, and a predefined high range.

Example 39 includes the method of example 32, wherein each of the plurality of data values include an associated timestamp; and the method includes determining, by the first application, that a time duration between a current time and the timestamps meets a predetermined amount of delay; and delaying the providing the second set of data to a second application for the predetermined amount of delay.

Example 40 includes the method of example 39, wherein the delay is between five minutes and three hours.

Example 41 includes the method of example 39, further including encrypting the second set of data prior to the providing the second set of data to the second application.

In some embodiments of the present technology (example 42), a method for controlling access to data relating to glucose levels on a mobile computing device includes receiving data relating to glucose levels using a first application operable on a smart phone; encrypting at least a subset of the data; providing the encrypted subset of data to a second application operable on the smart phone; providing the encrypted subset of data to a third application operable on the smart phone via the second application; and providing a key to the third application to decrypt the encrypted subset of data.

Example 43 includes the method of example 42, wherein the first application includes a medical device software application that configures the mobile computing device to receive and process the data relating to the glucose levels provided by a continuous glucose monitoring sensor device, and wherein one or both of the second application and the third application is a third-party software application.

Example 44 includes the method of example 43, wherein the third-party software application is configured to provide at least some capabilities different than that of the first application including processing ancillary data and integrating the ancillary data with the glucose data, wherein the ancillary data includes one or more of insulin data, meal data, or exercise data.

Example 45 includes the method of example 43, wherein the third-party software application is not an approved medical device software application approved by a governmental regulatory institution authorized to regulate medical device technologies.

Example 46 includes the method of example 42, in which the method further includes, prior to the providing the encrypted subset of data to the second application, separating the data into a first data set of the data and a second data set of the data consisting of the subset according to a predetermined criteria, wherein the first set of data comprises data values restricted from the second set of data.

Example 47 includes the method of example 42, wherein the received data includes glucose values and an associated timestamp for each glucose value; and the method includes determining, by the first application, that a time duration between a current time and the timestamps meets a predetermined amount of delay; and delaying the providing the second set of data to a second application for the predetermined amount of delay.

Example 48 includes the method of example 47, wherein the delay is between five minutes and three hours.

Example 49 includes the method of example 42, wherein the second application is provided the key to decrypt the encrypted subset of data.

In some embodiments of the present technology (example 50), a medical device software application for managing glucose data received from a glucose sensor is disclosed. The medical device software application is on a computer-readable medium of a mobile computing device, and includes instructions which, when executed by a processor of the mobile computing device, causes the mobile computing device to receive one or more glucose measurements generated by the glucose sensor; divide the one or more glucose measurements into a first set of data and a second set of data according to a predetermined criteria, the first set of data comprising data values restricted from the second set of data; and provide the second set of data to a third-party software application operable on the mobile computing device.

Example 51 includes the medical device software application of example 50, wherein the third-party software application is not an approved medical device software application approved by a governmental regulatory institution authorized to regulate medical device technologies.

Example 52 includes the medical device software application of example 50, wherein the third-party software application is configured to provide at least some capabilities different than that of the medical device software application including processing ancillary data and integrating the ancillary data with the retrospective glucose data, wherein the ancillary data includes one or more of insulin data, meal data, or exercise data.

Example 53 includes the medical device software application of example 50, wherein the received one or more glucose measurements include an associated timestamp, and wherein the medical device software application includes instructions, which when executed by the processor causes the mobile computing device to assign the received one or more glucose measurements as retrospective glucose data or actionable glucose data based on a predetermined amount of time difference between the timestamp and a current time; and provide the retrospective glucose data to a third-party software application operable on the mobile computing device.

Example 54 includes the medical device software application of example 50, wherein the medical device software application includes instructions, which when executed by the processor, causes the mobile computing device to encrypt the received one or more glucose measurements or the second set of data prior to providing the second set of data to the third-party software application; transmit an instruction for the third-party software application to provide the encrypted second set of data to a second third-party software application operable on the mobile computing device; and provide a key to the second third-party software application to decrypt the encrypted retrospective glucose data.

While this specification contains many specific implementation details, these should not be construed as limitations on the claims. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

What is claimed is:

1. A method for controlling distribution of data relating to glucose levels between applications executing on a computing device, comprising:
    receiving, at a mobile computing device, a plurality of data values relating to glucose level monitoring;
    separating, at a first application stored and executing at the mobile computing device, the plurality of data values into a first set of data and a second set of data according to a predetermined criteria, the first set of data comprising data values restricted from the second set of data; and
    providing the second set of data to a second application executing at the mobile computing device.

2. The method of claim 1, wherein the first application includes a medical device software application that configures the mobile computing device to receive and process glucose data including the data values relating to the glucose level monitoring provided by a continuous glucose monitoring sensor device, and wherein the second application includes a third-party software application.

3. The method of claim 2, wherein the third-party software application is configured to provide at least some capabilities different than that of the first application including processing ancillary data and integrating the ancillary data with the glucose data, wherein the ancillary data includes one or more of insulin data, meal data, or exercise data.

4. The method of claim 2, wherein the third-party software application is not an approved medical device software application approved by a governmental regulatory institution authorized to regulate medical device technologies.

5. The method of claim 1, wherein the plurality of data values are separated into the first set of data and the second set of data based on predetermined data permissions associated with the second application.

6. The method of claim 1, wherein the received plurality of data values include continuously generated glucose measurements, and wherein the separating the plurality of data values further includes:
averaging the continuously generated glucose measurements over a predetermined interval to produce glucose average values to be in the second set of data.

7. The method of claim 1, wherein the received plurality of data values include continuously generated glucose measurements, and wherein the separating the plurality of data values further includes:
generating generalized indications of the continuously generated glucose measurements over a predetermined interval to be in the second set of data, wherein a generalized indication is representative of the continuously generated glucose measurements being in one of a predefined low range, a predefined normal range, and a predefined high range.

8. The method of claim 1, wherein each of the plurality of data values include an associated timestamp; and the method comprises:
determining, by the first application, that a time duration between a current time and the timestamps meets a predetermined amount of delay; and
delaying the providing the second set of data to a second application for the predetermined amount of delay.

9. The method of claim 8, wherein the delay is between five minutes and three hours.

10. The method of claim 8, further comprising:
encrypting the second set of data prior to the providing the second set of data to the second application.

11. The method of claim 1, wherein the first application is configured to process glucose data associated with a continuous analyte sensor device; and the method further comprising:
receiving from a third-party application, at the first application, one or more single glucose measurements acquired from a single-measurement glucose sensor device;
analyzing, by the first application, metadata corresponding to the one or more single glucose measurements; and
authenticating, by the first application, the one or more single glucose measurements as calibration data for the continuous analyte sensor device.

12. A method for controlling access to data relating to glucose levels on a mobile computing device, comprising:
receiving data relating to glucose levels using a first application stored and executing at a smart phone;
separating the data into a first set of data and a second set of data according to a predetermined criteria;
encrypting at least the second set of data to generate an encrypted second set of data;
providing the encrypted second set of data to a second application executing at the smart phone;
providing the encrypted second set of data to a third application executing at the smart phone via the second application; and
providing a key to the third application to decrypt the encrypted second set of data.

13. The method of claim 12, wherein the first application includes a medical device software application that configures the mobile computing device to receive and process the data relating to the glucose levels provided by a continuous glucose monitoring sensor device, and wherein one or both of the second application and the third application is a third-party software application.

14. The method of claim 13, wherein the third-party software application is configured to provide at least some capabilities different than that of the first application including processing ancillary data and integrating the ancillary data with the glucose data, wherein the ancillary data includes one or more of insulin data, meal data, or exercise data.

15. The method of claim 13, wherein the third-party software application is not an approved medical device software application approved by a governmental regulatory institution authorized to regulate medical device technologies.

16. The method of claim 12, wherein the received data includes glucose values and an associated timestamp for each glucose value; and the method comprises:
determining, by the first application, that a time duration between a current time and the timestamps meets a predetermined amount of delay; and
delaying the providing the second set of data to a second application for the predetermined amount of delay.

17. The method of claim 16, wherein the delay is between five minutes and three hours.

18. The method of claim 12, wherein the second application is provided the key to decrypt the encrypted second set of data.

19. A medical device software application on a computer readable medium of a mobile computing device, the medical device software application for managing glucose data received from a glucose sensor, and comprising instructions which, when executed by a processor of the mobile computing device, causes the mobile computing device to:
receive, by the medical device software application, one or more glucose measurements generated by the glucose sensor;
divide, by the medical device software application stored and executing at the mobile computing device, the one or more glucose measurements into a first set of data and a second set of data according to a predetermined criteria, the first set of data comprising data values restricted from the second set of data; and
provide, by the medical device software application, the second set of data to a third-party software application executing at the mobile computing device.

20. The medical device software application of claim 19, wherein the third-party software application is not an approved medical device software application approved by a governmental regulatory institution authorized to regulate medical device technologies.

21. The medical device software application of claim 19, wherein the third-party software application is configured to provide at least some capabilities different than that of the medical device software application including processing ancillary data and integrating the ancillary data with retrospective glucose data, wherein the ancillary data includes one or more of insulin data, meal data, or exercise data.

22. The medical device software application of claim 19, wherein the received one or more glucose measurements include an associated timestamp, and wherein the medical device software application includes instructions, which when executed by the processor causes the mobile computing device to:

assign the received one or more glucose measurements as retrospective glucose data or actionable glucose data based on a predetermined amount of time difference between the timestamp and a current time; and provide the retrospective glucose data to a third-party software application executing at the mobile computing device.

23. The medical device software application of claim 19, wherein the medical device software application includes instructions, which when executed by the processor, causes the mobile computing device to:

encrypt the received one or more glucose measurements or the second set of data prior to providing the second set of data to the third-party software application to generate an encrypted second set of data;

transmit an instruction for the third-party software application to provide the encrypted second set of data to a second third-party software application executing at the mobile computing device; and provide a key to the second third-party software application to decrypt the encrypted second set of data.

24. The method of claim 1, wherein the first set of data includes real-time glucose measurements and the second set of data includes retrospective glucose measurements but does not include the real-time glucose measurements.

25. The method of claim 24, wherein the first set of data further includes predicted glucose measurements and the second set of data does not include the predicted glucose measurements.

26. The method of claim 1, wherein the first set of data includes real-time glucose measurements and the second set of data includes averaged glucose values over defined intervals but does not include the real-time glucose measurements.

27. The method of claim 1, wherein the first set of data includes real-time glucose measurements and the second set of data includes generalized indications of glucose levels but does not include the real-time glucose measurements.

* * * * *

UNITED STATES PATENT AND TRADEMARK OFFICE
CERTIFICATE OF CORRECTION

PATENT NO. : 10,945,600 B2
APPLICATION NO. : 15/019881
DATED : March 16, 2021
INVENTOR(S) : Michael Robert Mensinger et al.

Page 1 of 1

It is certified that error appears in the above-identified patent and that said Letters Patent is hereby corrected as shown below:

In the Specification

In Column 8, Line 12, delete "concentration" and insert -- concentration- --.

In Column 9, Line 33, delete "or/or" and insert -- and/or --.

In Column 35, Line 40, delete "examples" and insert -- examples. --.

In Column 38, Line 25, delete "range" and insert -- range. --.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*